US007897178B2

(12) United States Patent
Hata et al.

(10) Patent No.: US 7,897,178 B2
(45) Date of Patent: Mar. 1, 2011

(54) WATER-SWELLABLE CLAY MINERAL LAMINATED POWDER, DYE/WATER-SWELLABLE CLAY MINERAL COMPLEX AND COMPOSITION COMPRISING THE SAME

(75) Inventors: Hideo Hata, Yokohama (JP); Tomoyuki Katsuyama, Yokohama (JP)

(73) Assignee: Shiseido Co., Ltd., Chuo-ku, Tokyo (JP)

( * ) Notice: Subject to any disclaimer, the term of this patent is extended or adjusted under 35 U.S.C. 154(b) by 1635 days.

(21) Appl. No.: 10/541,772

(22) PCT Filed: Jan. 8, 2004

(86) PCT No.: PCT/JP2004/000058

§ 371 (c)(1),
(2), (4) Date: Jul. 8, 2005

(87) PCT Pub. No.: WO2004/063286

PCT Pub. Date: Jul. 29, 2004

(65) Prior Publication Data

US 2006/0110344 A1 May 25, 2006

(30) Foreign Application Priority Data

Jan. 8, 2003 (JP) .............................. 2003-002623
May 9, 2003 (JP) .............................. 2003-131828
May 9, 2003 (JP) .............................. 2003-131829

(51) Int. Cl.
*A61K 9/16* (2006.01)
(52) U.S. Cl. ..................................... 424/490; 106/31.28
(58) Field of Classification Search .................. 424/490; 106/31.28
See application file for complete search history.

(56) References Cited

U.S. PATENT DOCUMENTS

2003/0163877 A1* 9/2003 Baker et al. ..................... 8/405

FOREIGN PATENT DOCUMENTS

| JP | 56-103105 | | 8/1981 |
| JP | 358124713 A | * | 7/1983 |
| JP | 6039574 | | 5/1994 |
| JP | 11 116837 | | 4/1999 |
| JP | 11116837 | * | 4/1999 |

OTHER PUBLICATIONS van Duffel et al., "Multilayered Clay Films: Atomic Force Microscopy Study and Modeling", 1999, Langmuir, vol. 15 No. 22, pp. 7520-7529.*
Brief Description of Relevance for JP56-103105B, one page.
Japanese Patent Abstract Publication No. 56-103105 published Aug. 18, 1981, one page.
Japanese Patent Abstract Publication No. 07-216256 published Aug. 15, 1995, two pages.
Japanese Patent Abstract Publication No. 63-090573 published Apr. 21, 1988, one page.
Japanese Patent Abstract for Publication No. 03-139569 published Jun. 13, 1991.
Japanese Patent Abstract for Publication No. 11-116837 published Apr. 27, 1999.
Iler, "Multilayers of Colloidal Particles," Journal of Colloid and Interface Science 21, pp. 569-594 (1966).
Lee et al., "Inorganic Analogues of Langmuir-Blodgett Films: Adsorption of Ordered Zirconium 1-10-Decanebisphosphonate . . . " J. Am. Chem. Soc. 1988, 110, pp. 618-620.
Decher et al., "Proof of multilayer structural organization in self-assembled polycation-polyanion molecular films," Thin Solid Films, 344 (1994) pp. 772-777.
Kleinfeld et al., "Stepwise Formation of Multilayered Nanostructural Films from Macromolecular Precursors," Science, vol. 265, Jul. 15, 1994, pp. 370-373.
Lvov et al., "Formation of Ultrathin Multilayer and Hydrated Gel from Montmorillonite and Linear Polycations," Langmuir 1966, 12, pp. 3038-3044.
Kotov et al., "Layer-by-Layer Self-Assembly of Alumosilicate-Polyelectrolyte Composites: Mechanisms of Deposition . . . " Chem. Mater. 1998, 10, pp. 886-895.
van Duffel et al., "Multilayered Clay Films: Atomic Force Microscopy Study and Modeling," Langmuir 1999, 15 pp. 7520-7529.
Rouse, "Sol-Gel Processing of Ordered Multilayers to Produce Composite Films of Controlled Thickness," Chem. Mater. 2000, 12, pp. 2502-2507.
Kim et al., "Layered Aluminosilicate/Chromophore Nanocomposites and Their Electrostatic Layer-by-Layer Assembly," Chem. Mater. 2001, 13, pp. 243-246.
European Patent Office, The extended European search report, Mar. 29, 2010, (7 pages).

* cited by examiner

*Primary Examiner* — Karlheinz R Skowronek
*Assistant Examiner* — Ali Soroush
(74) *Attorney, Agent, or Firm* — Rankin, Hill & Clark LLP

(57) ABSTRACT

The water-swellable clay mineral laminated powder of the present invention is characterized in that a layer of ionic molecule having two or more ionic functional group is laminated on the surface of a base powder particle, and a layer of water-swellable clay mineral is laminated thereon, and the layers are sequentially laminated so that the surface charge or the ionic charge of each layer is alternately positive and negative. The water-swellable clay mineral laminated powder of the present invention can impart new functionalities to the base powder easily, as a result of that the water-swellable clay mineral is stably laminated on the surface of the base powder.

And the dye/water-swellable clay mineral complex of the present invention is characterized in that polybase and/or nonionic hydrophilic polymer and dye are complexed to water-swellable clay mineral. The dye/water-swellable clay mineral complex of the present invention is excellent for various resistance characteristics of the dye such as dissolution resistance, lightfastness, and chlorine resistance. In addition, the dye/water-swellable clay mineral complex is very useful as a water-type coloring agent since it has excellent coloring abilities, clearness, and dye fastness in water.

8 Claims, 5 Drawing Sheets

WATER-SWELLABLE CLAY MINERAL LAMINATED POWDER, DYE/WATER-SWELLABLE CLAY MINERAL COMPLEX AND COMPOSITION COMPRISING THE SAME

RELATED APPLICATIONS

This application claims the priority of Japanese Patent Application No. 2003-2623 filed on Jan. 8, 2003, Japanese Patent Application No. 2003-131828 filed on May 9, 2003, and Japanese Patent Application No. 2003-131829 filed on May 9, 2003, which are incorporated herein by reference.

BACKGROUND OF THE INVENTION

1. Field of the Invention

The present invention relates to new water-swellable clay mineral laminated powder, dye/water-swellable clay mineral complex, and the compositions comprising the same, and in particular, relates to the impartment of functionality to the base powder and the tolerance improvement of dye in the dye/water-swellable clay mineral complex.

2. Prior Art

In the past, various laminated powders with various functionalities, which cannot be achieved by the base powder itself, have been prepared by depositing different kinds of powder particles, metal oxides, or organic compounds, etc. on the surface of the base powder. Pearlescent pigment, in which flaky mica is laminated with titanium dioxide, is a typical example of laminated powder; the pearlescent pigment expresses an interference color.

On the other hand, water-swellable clay mineral is known to form a complex with various organic compounds. Water-swellable clay mineral has a structure in which plate crystals are stacked, and cations and water molecules are sandwiched between them. Thus, a complex can be easily prepared by adsorbing molecules on the cations or by intercalating molecules by replacing the interlayer cations or water molecules. Examples of the complex with water-swellable clay mineral include a complex with a cationic molecule such as cationic dye or n-alkylamine salt; and a complex with a polar molecule such as alcohol, ketone, ether, nitrile, or water-soluble polymer. In this way, it is possible to impart various functionalities to a water-swellable clay mineral by complexing various functional molecules.

We may increase the possibility of imparting functionalities to the base powder by using, as the foundation for attaching functional molecules, the water-swellable clay mineral laminated on the surface of the base powder. However, this type of water-swellable clay mineral laminated powder has not been reported.

On the other hand, by the LbL method, which has been actively investigated in recent years, a base material with the opposite charge to that of the base material is successively adsorbed in a dilute aqueous solution or dispersion by electrostatic interaction. Thus, a multilayer laminate structure can be relatively easily constructed. In this technology, it was discovered by Iler in 1966 that colloid particles of opposite charges can be alternately and successively adsorbed (Iler: Journal of Colloid and Interface Science, 1966, 21, p. 569-594). In 1988, alternating adsorption of $Zr^{4+}$ and diphosphonic acid was reported by Mallouk et al. (Mallouk et. al: Journal of American Chemical Society, 1988, 110, p. 618-620). In addition, Decher et al. reported the formation of a multilayer film of polymer electrolytes (Decher et. al: Thin Solid Films, 1994, 244, p. 772-777). These discoveries have triggered numerous reports of laminate structures of various ion species and charged colloid particles.

Kleinfeld et al. reported, in 1994, a multilayer structure in which polymer electrolyte and water-swellable clay mineral were alternately laminated on a silicon wafer substrate (Kleinfeld et al.: Science, 1994, 265, p. 370-373). Later, Lvov et al., Kotov et al., Van Duffel et al., Rouse et al., and Kim et al. reported laminates of polymer electrolyte and water-swellable clay mineral (Lvov et al.: Langmuir, 1996, 12, p. 3038-3044; Kotov et al.: Chemistry Materials, 1998, 10, p. 886-895; Van Duffel et al.: Langmuir, 1999, 15, p. 7520-7529; Rouse et al.: Chemistry Materials, 2000, 12, p. 2502-2507; and Kim et al.: Chemistry Materials, 2001, 13, p. 243-246).

However, all these multilayer structures of polymer electrolyte and water-swellable clay mineral were prepared by the immersion of a base plate (size is in the order of cm) such as a silicon wafer or mica. A material in which water-swellable clay mineral laminated on the surface of the powder as base has not been reported.

As mentioned previously, various functionalities can be imparted to water-swellable clay mineral by complexing it with various functional molecules.

On the other hand, a dye has been used in cosmetics and various coloring applications because of its clear color rendering. However, the stability such as lightfastness and chlorine resistance has often been poor. Even lake pigment in which acid dye is supported on metal has a problem in lightfastness and chlorine resistance. There is also a problem in that dye leaches out of the lake pigment. Many water-soluble dyes including acid dye and basic dye are also weak against external factors such as chlorine in water.

As an example of pigment in which dye and water-swellable clay mineral are complexed, there is a pigment in which dye is adsorbed on a complex of chitosan and swellable smectite; it is reported that this pigment has good dispersibility (Japanese Unexamined Patent Publication H03-139569). It is also reported that a complex containing dye, a linear polycation without cyclic sugar structure, and a layered clay mineral has excellent lightfastness and excellent dissolution resistance (Japanese Unexamined Patent Publication H11-116837).

In order to use chitosan in solution, however, it is necessary to use a solvent of acidic pH; thus, usable dyes are limited. The polycation used in Japanese Unexamined Patent Publication H11-116837 is an amine-type, such as polyethyleneimine, which contains a primary amino group. Therefore, it is also affected by pH. In addition, there has been a problem, in both cases, in that the content of the dye in the pigment is not sufficient, or that it is necessary to finely pulverize them to achieve sufficient color rendering. Furthermore, since the refractive index of clay mineral itself is ca. 1.5, there is a limit in the coloring abilities and hiding power of the pigment. It is also difficult to use the pigment as a substitute for an acid dye because of an in-water dispersion problem.

SUMMARY OF THE INVENTION

The present inventors have diligently researched in consideration of the above problem. As a result, the inventors have discovered that laminated powder, in which water-swellable clay mineral is stably laminated on the base powder, can be obtained by adsorbing an ionic molecule having two or more ionic functional group on the surface of the base powder, thus increasing the charge density of the powder surface and controlling the charge of the powder surface, and by adsorbing water-swellable clay mineral with the opposite charge to the ionic charge on the powder surface. According to this method, new functionalities can be easily imparted to the powder by adsorbing functional molecules on the surface of the water-swellable clay mineral that is laminated on the powder or by intercalating functional molecules between the layers of water-swellable clay mineral.

The present inventors have also investigated, in more detail, the complexation of water-swellable clay mineral and dye. As a result, it was discovered that a dye/water-swellable clay mineral complex, in which polybase and/or nonionic hydrophilic polymer and dye are complexed to the water-swellable clay mineral, has various excellent resistance properties such as dye dissolution resistance, lightfastness, and chlorine resistance. It was also discovered that this dye/water-swellable clay mineral complex is very useful as a water-type coloring agent since it is excellent in coloring abilities, clearness, and dye fastness in water, thus leading to completion of the present invention.

More specifically, the water-swellable clay mineral laminated powder in the present invention is characterized in that a layer of ionic molecule having two or more ionic functional group is laminated on the surface of a base powder particle, a layer of water-swellable clay mineral is laminated thereon, and the layers are sequentially laminated so that the surface charge or the ionic charge of each layer is alternately positive and negative.

It is preferable that the ionic molecule is a polymer electrolyte. It is also preferable that the primary particle diameter of the water-swellable clay mineral is 0.5 µm or less. It is also preferable that the average particle diameter of the base powder is 0.1 to 1000 µm.

It is also preferable that a functional molecule, which having opposite charge to the surface charge of outermost water-swellable clay mineral or the ionic charge of outermost ionic molecules, is adsorbed on the outermost surface of the laminated powder. It is also preferable that the water-swellable clay mineral is located on the outermost surface of the laminated powder, and a cationic functional molecule is adsorbed to the ion exchange group on the surface of the water-swellable clay mineral on the outermost surface.

It is also preferable that the cationic functional molecule is an alkyl ammonium salt. It is also preferable that the amount of the adsorbed cationic functional molecule in the laminated powder is 0.01 to 10 weight %. It is also preferable that the water-swellable clay mineral is a water-swellable clay mineral in which other molecules intercalated in between the layers of the water-swellable clay mineral.

It is also preferable that the water-swellable clay mineral is a water-swellable clay mineral in which polyhydric alcohol intercalated in between the layers of the water-swellable clay mineral. It is also preferable that the water-swellable clay mineral is a water-swellable clay mineral in which water-soluble polymer intercalated in between the layers of the water-swellable clay mineral.

It is also preferable that the water-swellable clay mineral is a dye/water-swellable clay mineral complex in which dye and water-swellable clay mineral are complexed.

It is also preferable that the dye/water-swellable clay mineral complex is a complex in which polybase and/or nonionic hydrophilic polymer and dye are complexed to water-swellable clay mineral.

It is also preferable that the dye/water-swellable clay mineral complex is a complex in which polybase and acid dye are intercalated in between the layers of the water-swellable clay mineral. It is also preferable that the polybese is a polybase having quaternary ammonium group in the molecule.

It is also preferable that the dye/water-swellable clay mineral complex is a complex in which nonionic hydrophilic polymer and water-soluble dye are complexed to water-swellable clay mineral. It is also preferable that the dye/water-swellable clay mineral complex is a complex in which nonionic hydrophilic polymer and water-soluble dye are intercalated in between the layers of the water-swellable clay mineral. It is also preferable that the water-soluble dye is an acid dye.

The producing method of the water-swellable clay mineral laminated powder in the present invention is characterized in that the method comprises; an ionic molecule adsorption process for an ionic molecule is adsorbed on a base powder surface, wherein a base powder particle is dispersed in an aqueous solution of an ionic molecule having two or more ionic functional group with the opposite charge to the charge of the base powder; and a water-swellable clay mineral adsorption process for a water-swellable clay mineral is adsorbed on the powder surface, wherein the powder particle after the adsorption of the ionic molecule is dispersed in an aqueous solution of the water-swellable clay mineral having opposite charge to the ionic charge of the ionic molecule of the powder particle surface.

The cosmetic in the present invention are characterized in that the cosmetic comprises the water-swellable clay mineral laminated powder.

The dye/water-swellable clay mineral complex in the present invention is characterized in that polybase and/or nonionic hydrophilic polymer and dye are complexed to water-swellable clay mineral.

It is preferable that polybase and acid dye are intercalated in between the layers of the water-swellable clay mineral. It is also preferable that the polybese is a polybase having quarternary ammonium group in the molecule.

It is also preferable that nonionic hydrophilic polymer and water-soluble dye are complexed to water-swellable clay mineral. It is also preferable that nonionic hydrophilic polymer and water-soluble dye are intercalated in between the layers of the water-swellable clay mineral. It is also preferable that the water-soluble dye is an acid dye.

It is also preferable that the primary particle diameter of the water-swellable clay mineral is 1 µm or less.

The pigment composition in the present invention is characterized in that the pigment composition comprises the dye/water-swellable clay mineral complex.

The water-based coloring agent in the present invention is characterized in that the water-based coloring agent consists of the dye/water-swellable clay mineral complex.

The water-based composition in the present invention is characterized in that the water-based composition contains the dye/water-swellable clay mineral complex.

The water-based cosmetics in the present invention are characterized in that the water-based cosmetics comprises the dye/water-swellable clay mineral complex.

The acid dye laminate pigment in the present invention is characterized in that a dye/water-swellable clay mineral complex, which having opposite charge to the charge of a base powder, is coated on the surface of the base powder, and a polybase and an acid dye are intercalated in between the layers of the water-swellable clay mineral of the dye/water-swellable clay mineral complex. The acid dye laminate pigment in the present invention is also characterized in that one or more layer of the acid dye /water-swellable clay mineral complex is further laminated on the surface of the acid dye laminated pigment, and a layer of an ionic molecule, which having opposite surface charge to the charge of the acid dye/water-swellable clay mineral complex, exists in between the each layers of the acid dye/water-swellable clay mineral complex.

It is also preferable that t the primary particle diameter of the water-swellable clay mineral is 1 μm or less. It is also preferable that the average particle diameter of the base powder is 0.1 to 1000 μm. It is also preferable that the surface of the acid dye laminated pigment is further treated to be hydrophobic.

The producing method of the acid dye laminate pigment of the present invention is characterized in that the method comprises comprising; an acid dye/water-swelling clay mineral complex producing process for an acid dye is intercalated in between the layers of the water-swellable clay mineral, wherein a polybase and an acid dye is contacted to a water-swellable clay mineral in aqueous phase; and laminating process for the acid dye/water-swelling clay mineral complex is electrostatically adsorbed on the surface of a base powder, wherein obtained acid dye/water-swelling clay mineral complex and a base powder, which having opposite charge to the charge of the complex, are mixed in aqueous phase.

The pigment composition of the present invention is characterized in that the pigment composition comprises the acid dye laminate pigment.

The cosmetic of the present invention are characterized in that the cosmetic comprises the acid dye laminate pigment.

DESCRIPTION OF THE PREFERRED EMBODIMENT

1. Water-Swellable Clay Mineral Laminated Powder

Figure 1:
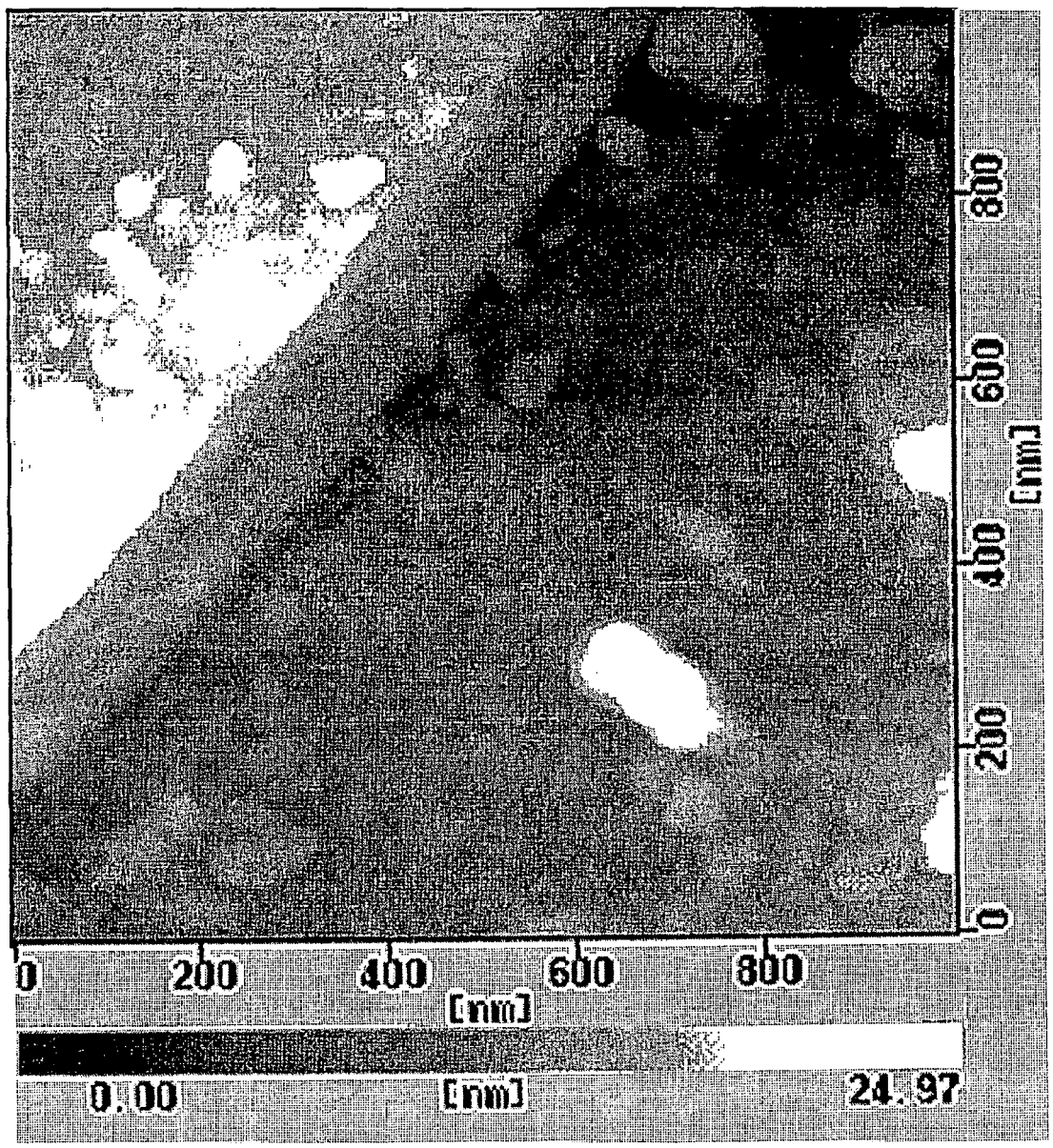
FIG. 1 shows a DFM image of synthetic fluorphlogopite.

Initially, water-swellable clay mineral laminated powder of the present invention is explained.

Water-swellable clay mineral laminated powder of the present invention can be obtained by sequentially laminating ionic molecules and water-swellable clay mineral, so that positive and negative charges are alternating on the surface of any base powder. Thus, water-swellable clay mineral can be uniformly and stably coated on the surface of the base powder, imparting new functionalities to the base powder. In addition, by using the laminated clay mineral as the foundation, more functional molecules can be adsorbed on the surface, or functional molecules can be intercalated between the layers of the laminated clay mineral; thus, excellent functionalities can be imparted.

The water-swellable clay mineral laminated powder in the present invention is prepared by laminating water-swellable clay mineral and ionic molecules on the base powder by electrostatic interaction. Generally, not only powder but also solid surface is positively or negatively charged in an aqueous solution. Therefore, the base powder used in the present invention is not limited to any special kind of powder. So far as the effect of the present invention is not undermined, any powder can be used.

Examples of the base powder that can be used in the present invention include talc, kaolin, mica, sericite, muscovite, phlogopite, synthetic mica, lepidolite, biotite; and lepidolite, calcined clay minerals such as vermiculite, calcined mica, calcined talc, and calcined sericite; inorganic powders such as magnesium carbonate, calcium carbonate, aluminum silicate, barium silicate, calcium silicate, magnesium silicate, strontium silicate, metal tungstate, magnesium, silica, zeolite, glass, barium sulfate, calcined calcium sulfate (calcined gypsum), calcium phosphate, fluoroapatite, hydroxyapatite, ceramic powder, metallic soap (zinc myristate, calcium palmitate, aluminum stearate, etc.), and graphite boron nitride, organic powders such as PMMA, silicone resin powder, nylon powder, silk powder, wool powder, urethane powder, and PTFE; inorganic white pigments such as titanium dioxide and zinc oxide; inorganic red pigments such as iron oxide (rouge) and iron titanate; inorganic brown pigments such as γ-iron oxide; inorganic yellow pigments such as yellow iron oxide and loess; inorganic black pigments such as black iron oxide, carbon black, and low oxidation titanium oxide; inorganic violet pigments such as manganese violet and cobalt violet; inorganic green pigments such as chromium oxide, chromium hydroxide, and cobalt titanate; inorganic blue pigments such as ultramarine and Prussian blue; inorganic pearlescent pigments such as titanium oxide coated mica, titanium oxide coated bismuth oxychloride, titanium oxide coated talc, colored titanium oxide coated mica, bismuth oxychloride, and fish scale flake; metal powder pigments such as aluminum powder and copper powder; organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404; organic lake pigments: zirconium lakes, barium lakes, and aluminum lakes, such as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No.1; and natural pigments such as chlorophyll and β-carotene.

The preferable average particle diameter of the base powder used in the present invention is 0.1 to 1000 μm.

For the water-swellable clay mineral used in the water-swellable clay mineral laminated powder of the present invention, there is no special limitation. One example of the water-swellable clay mineral is layered silicate minerals of the smectite group. These layered silicate minerals of the smectite group are montmorillonite, beidellite, nontronite, saponite, hectorite, etc., and either natural minerals or synthetic minerals can be used in the present invention. Examples of commercially available water-swellable clay minerals include Kunipia, Smecton (Kunimine Industries), Veegum (R.T. Vanderbilt Company), Laponite (Laporte Industries), and tetrasilicic fluorine mica. As the water-swellable clay mineral of the present invention, one or more species can be arbitrarily selected from the layered silicates of the smectite group. As for the water-swellable clay mineral in the present invention, small primary particles are more desirable. A primary particle diameter of 0.5 μm or less is preferable. The most preferable is Laponite of which the primary particle diameter is ca. 20 nm. When the above water-swellable clay mineral is laminated on the surface of any base powder, an aqueous dispersion of the above water-swellable clay mineral is used at a concentration where the gelation does not take place.

An ionic molecule used in the water-swellable clay mineral laminated powder of the present invention is an ionic molecule having two or more ionic functional group, and there is no other special limitation. As for the ionic molecule used in the present invention, a polymer electrolyte is especially preferable from a standpoint of its adsorption strength to the surface of the base. A polymer electrolyte usually has ionic functional groups in the constituents of the polymer chain or on the substituents. So far as the polymer electrolyte is as such, it can be used without limitation in the present invention. However, a linear and/or water-soluble polymer electrolyte is desirable.

Polymer electrolyte can be classified to polyacid and polybase depending upon the ionic functional group. A polyacid ionizes to a polyanion by releasing protons. The examples of polyacids include polyphosphoric acid, polyvinyl or polystyrene sulfuric acid, polyvinyl or polystyrene sulfonic acid, and polyvinyl carboxylic acid. The examples of their salts include polyphosphate, polysulfate, polysulfonate, polyphosphonate, polyacrylate, and polycarbonate.

Examples of polybase include polyamines such as polyethylene amine, polyvinyl amine, polyvinyl pyridine; and polyammonium salts such as poly(dimethyldiallylammonium chloride) (PDDA). When the above ionic molecule is laminated on the surface of any base powder, the above ionic molecule is used in an aqueous dispersion of a suitable concentration.

In the water-swellable clay mineral laminated powder of the present invention, as a functional molecule that is adsorbed on the water-swellable clay mineral, which has been laminated on the surface of the base powder, a functional molecule with a positive charge, for example, a functional molecule with a cationic functional group is preferably used since the water-swellable clay mineral often has a negative charge. Examples of cationic functional molecules include tetraalkyl ammonium salt and perfluoroalkyl ammonium salt. The most preferable are tetraalkyl ammonium salts represented by the following general formula (1). The preferred amount of the adsorbed cationic functional molecule in the present invention is 0.01 to 10 weight %.

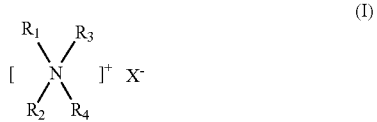

(In the formula, X is a chlorine atom or a bromine atom; $R_1$ is a linear alkyl group having 10 to 22 carbon atoms, and $R_2$, $R_3$, and $R_4$ are linear alkyl groups having 1 to 10 carbon atoms; or $R_1$ and $R_2$ are linear alkyl groups having 10 to 22 carbon atoms, and $R_3$ and $R_4$ are linear alkyl groups having 1 to 10 carbon atoms.)

In the present invention, as other molecules that are intercalated in the water-swellable clay mineral, water-soluble polymer and polyhydric alcohol, for example, are preferably used from a viewpoint of imparting functionalities.

Examples of water-soluble polymer that is intercalated between the layers of the water-swellable clay mineral in the water-swellable clay mineral laminated powder of the present invention include poly(vinyl alcohol) (PVA), poly(vinyl pyrrolidone) (PVP), polyethylene glycol (PEG), polysaccharides such as hyaluronic acid and chitosan; and polybases such as poly(dimethyldiallylammonium chloride) (PDDA). The degree of polymerization of each water-soluble polymer is wide-ranging. However, there is no limitation in use for all cases of the present invention.

Examples of polyhydric alcohol that is intercalated between the layers of the water-swellable clay mineral in the water-swellable clay mineral laminated powder of the present invention include glycerin, di(propylene glycol), 1,3-butylene glycol, etc.

As a dye used in the water-swellable clay mineral laminated powder of the present invention, any dye that is complexable to the water-swellable clay mineral is relevant. Examples of the dye include Food Yellow No. 4 (Tartrazine), Yellow No. 5 (Sunset Yellow FCF), Yellow No. 203 (Quinoline Yellow WS), Blue No. 1 (Brilliant Blue FCF), Red No. 3 (Erythrosine), Red No. 401 (Violamine R), Red No. 213 (Rhodamine B), Violet No. 201 (Alizurine Purple SS), Red No. 225 (Sudan III), carminic acid, laccaic acid, carthamin, shikonin, chlorophyllins, etc.

In the water-swellable clay mineral laminated powder of the present invention, from a viewpoint of dye fastness, a dye/water-swellable clay mineral complex, in which polybase and/or nonionic hydrophilic polymer and dye are complexed to the water-swellable clay mineral, can be preferably used.

As for such a dye/water-swellable clay mineral complex, an acid dye/water-swellable clay mineral complex, in which polybase and acid dye are complexed to the water-swellable clay mineral, is especially preferable. As for a polybase, a molecule having quaternary ammonium groups is desirable.

In addition, as for a dye/water-swellable clay mineral complex, a water-soluble dye/water-swellable clay mineral complex, in which nonionic hydrophilic polymer and water-soluble dye are complexed to the water-swellable clay mineral, is especially preferable. As for a water-soluble dye, an acid dye is desirable.

These dye/water-swellable clay mineral complexes will be explained in detail below.

In addition to the above-described essential component laminated powder, components usually used in cosmetics and pharmaceuticals can be blended in the cosmetics of the present invention to the extent that the effect of the present invention is not undermined. Examples of oil components include silicone oils such as dimethylpolysiloxane, cyclic dimethylpolysiloxane, and methylphenylpolysiloxane; various hydrocarbon oils such as squalane, liquid paraffin, light isoparaffin, vaseline, microcrystalline wax, ozokerite, and ceresin; higher fatty acids such as myristic acid, palmitic acid, stearic acid, oleic acid, isostearic acid, and behenic acid; higher alcohols such as cetyl alcohol, stearyl alcohol, oleyl alcohol, and batyl alcohol; esters such as cetyl 2-ethylhexanoate, 2-ethylhexyl palmitate, 2-octyldodecyl myristate, neopentyl glycol-2-ethylhexanoate, glyceryl trioctanoate, 2-octyldodecyl oleate, isopropyl myristate, myristyl myristate, glyceryl triisostearate, glyceryl trioleate, and glyceryl tricocoate; fats such as olive oil, avocado oil, jojoba oil, sunflower oil, safflower oil, camellia Japonica seed oil, shea butter, macadamia nut oil, mink oil, lanolin, lanolin acetate, lanolin oil, and castor oil; waxes such as Japan wax; and fluorinated oils such as perfluoropolyether and perfluorocarbon. Other examples include silicone resins such as trimethyl siloxysilicate and MDQ resin; film-forming polymers such as polymeric silicone rubber and acrylic-modified silicone copolymer; surfactant, UV absorber, antioxidant, salts, preservative, thickening agent, moisturizer, perfume, vitamin, hormone, whitening agent, and antiphlogistic agent.

There is no limitation for the use of cosmetics of the present invention so far as a cosmetic comprises the essential component, which is the above-described laminated powder. Examples of the cosmetic include make up cosmetic such as oil-based foundation, emulsion foundation, powdery foundation, dual-use foundation, face powder, blusher, pressed powder, cheek color, lipstick, eye liner, mascara, and eye shadow; examples also include skin care cosmetic such as milky lotion, lotion, cream, sunscreen, and pre-makeup.

2. Dye/Water-Swellable Clay Mineral Complex

The dye/water-swellable clay mineral complex of the present invention is explained in the following.

The dye/water-swellable clay mineral complex of the present invention is obtained by complexing polybase and/or nonionic hydrophilic polymer and dye to the water-swellable clay mineral.

Thus, various resistance characteristics of the dye such as dissolution resistance, lightfastness, and chlorine resistance are excellent since the dye is strongly adsorbed in the water-swellable clay mineral. In addition, this dye/water-swellable clay mineral complex is very useful as a water-type coloring agent since it has excellent coloring abilities, clearness, and dye fastness in water.

The dye/water-swellable clay mineral complex of the present invention is preferably an acid dye/water-swellable clay mineral complex, in which polybase and acid dye are complexed to the water-swellable clay mineral, or a water-soluble dye/water-swellable clay mineral complex, in which nonionic hydrophilic polymer and water-soluble dye are complexed to water-swellable clay mineral.

The acid dye/water-swellable clay mineral complex and the water-soluble dye/water-swellable clay mineral complex are respectively explained below.

2-1 Acid Dye/Water-Swellable Clay Mineral Complex

In the acid dye/water-swellable clay mineral complex of the present invention, polybase and acid dye are intercalated between the layers of water-swellable clay mineral.

The water-swellable clay mineral generally has a negative surface charge. Acid dye also has an anionic group such as the $SO_3^-$ group. Therefore, it is usually difficult to intercalate acid dye between the layers of water-swellable clay mineral by simply mixing them in water. Even if acid dye is adsorbed on the surface of the clay mineral, it is easily desorbed by washing. However, if polybase is intercalated between the layers of water-swellable clay mineral, acid dye can be easily intercalated between the layers. This is probably due to the increased cationic character of the interlayers of the water-swellable clay mineral because of the polybase. In this case, the intercalated acid dye is not easily desorbed by washing.

In the acid dye/water-swellable clay mineral complex of the present invention, a polybase containing quaternary ammonium groups ($R_4N^+$, R is a hydrocarbon group) in its structure is preferably used, and a linear water-soluble polymer electrolyte is preferred. Examples of the polybase include poly(dimethyldiallylammonium) and its salts; poly(methacrylamidopropyltrimethylammonium) and its salts; quaternarized poly(vinylpyridine) and its salts; and cationic polysaccharides (e.g. cationic cellulose, cationic guar gum, cationic roast bean gum, cationic β-1,3-glucan, cationic starch, etc.). They can be homopolymers or copolymers.

Among these, poly(dimethyldiallylammonium chloride) (PDDA) is especially preferable since it is a uniformly-charged, ideal, strong polybase and pH-independent. In addition, PDDA is a blendable component for cosmetics; thus, it is desirable from a safety standpoint.

These polybases have various molecular weights. In the present invention, there is no special limitation for the molecular weight so far as a polybase can provide a large enough charge to intercalate acid dye in the clay mineral. However, if the molecular weight of a polybase is large, the water-swellable clay mineral tends to flocculate when the polybase is intercalated between the layers of the water-swellable clay mineral. Therefore, the average molecular weight should preferably be one million or less; more preferably the average molecular weight should be 100 thousands or less.

When a polybase is intercalated in the water-swellable clay mineral, an aqueous solution of the polybase is usually used at an appropriate concentration.

As an acid dye usable in the acid dye/water-swellable clay mineral complex of the present invention, any dye can be used so far as it is intercalatable between the layers by its electrostatic interaction with the polybase. Specific examples include Red No. 2, Red No. 3, Red No. 102, Red No. 104-1, Red No. 105-1, Red No. 106, Yellow No. 4, Yellow No. 5, Green No. 3, Blue No. 1, Blue No. 2, Red No. 227, Red No. 230-1, Orange No. 205, Yellow No. 202-1, Yellow No. 203, Green No. 204, Blue No. 205, Brown No. 201, Red No. 401, Red No. 504, Orange No. 402, Yellow No. 403-1, Yellow No. 406, Yellow No. 407, Green No. 401, Violet No. 401, Black No. 401, etc. In addition, natural acid dyes such as carminic acid and laccaic acid can be used.

When an acid dye is intercalated in the water-swellable clay mineral, an aqueous solution of the acid dye is usually used at an appropriate concentration.

For the water-swellable clay mineral used in the present invention, there is no special limitation. Specific examples are layered silicate minerals of the smectite group, for example, montmorillonite, beidellite, nontronite, saponite, hectorite, etc., and either natural or synthetic minerals can be used. Examples of commercial product include Kunipia, Smecton (Kunimine Industries), Veegum (R. T. Vanderbilt Company), Laponite (by Laporte Industries), and tetrasilicic fluorine mica. In the practice of the present invention, one or more species can be arbitrarily selected from the layered silicates of the smectite group.

The primary particle diameter of the water-swellable clay mineral is preferably 1 μm or less, and more preferably 0.5 μm or less.

The higher the cation exchange capacity (CMC) of the water-swellable clay mineral, the larger the amount of intercalatable polybase and acid dye; thus, a higher cation exchange capacity is preferable. When polybase and acid dye are intercalated, or when the obtained acid dye/water-swellable clay mineral complex is coated on the base powder, clay mineral is used in an aqueous dispersion at a concentration where gelation does not take place.

The acid dye/water-swellable clay mineral complex can be prepared by allowing water-swellable clay mineral, polybase, and acid dye to contact each other in water. For example, an aqueous suspension is prepared by sufficiently dispersing a water-swellable clay mineral in water at a concentration where gelation does not take place (e.g. 1 to 5 weight %). A polybase aqueous solution is mixed with this suspension, and then an acid dye aqueous solution is added and mixed. The powder of the acid dye/water-swellable clay mineral complex can be obtained from the mixed solution after solid-liquid separation (centrifugal separation and etc.), washing, drying, and pulverizing as necessary. It is possible to add acid dye before polybase, or to add an aqueous mixed solution of polybase and acid dye to the aqueous suspension of the water-swellable clay mineral. However, it is preferable to add polybase to achieve sufficient intercalation before the addition of acid dye.

The mixing condition of polybase and acid dye to the water-swellable clay mineral can be appropriately selected depending upon raw materials etc. Mixing is usually conducted for 1 to 24 hours at room temperature.

The acid dye laminate pigment of the present invention was prepared by adsorbing the above obtained acid dye/water-swellable clay mineral complex, by electrostatic interaction, on the surface of the base powder with the opposite surface charge. The base powder was sequentially laminated with one or more layer by electrostatic interaction.

When the surface charge of the base powder was the same as the surface charge of the acid dye/water-swellable clay mineral complex, a layer of ionic molecules having two or more ionic functional group was formed on the powder surface. Thus, the base powder was allowed to have the opposite surface charge to that of the acid dye/water-swellable clay mineral complex.

The pigment in which two or more layer of the acid dye/water-swellable clay mineral complex is laminated on the surface of base powder is also an acid dye laminate pigment of the present invention. In this case, respective layers are laminated, by electrostatic interaction, by forming a layer with the opposite surface charge to that of the acid dye/water-swellable clay mineral complex between respective layers of the acid dye/water-swellable clay mineral complex. Specifically, a layer of the acid dye/water-swellable clay mineral complex is adsorbed on the surface of the base powder, and on this is adsorbed a layer of an ionic molecule with the opposite surface charge to that of the acid dye/water-swellable clay mineral complex. Thus, more layers of the acid dye/water-swellable clay mineral complex and layers of an ionic molecule can be alternately adsorbed by electrostatic interaction.

Accordingly, in the acid dye laminate pigment of the present invention, respective layers of the positive charge and negative charge are alternately and sequentially laminated.

"Surface charge" in the present invention is zeta potential (; potential) measured with LEZA60 (Otsuka Electronics) using a 0.1 M NaCl aqueous solution as the mobile phase solvent.

As the base powder of the present invention, any powder component can be used so far as the effect of the present invention is not undermined. Specific examples of the powder include talc, kaolin, mica, sericite, muscovite, phlogopite, synthetic mica, lepidolite, biotite, and lepidolite; calcined clay minerals such as vermiculite, calcined mica, calcined talc, and calcined sericite; inorganic powders such as magnesium carbonate, calcium carbonate, aluminum silicate, barium silicate, calcium silicate, magnesium silicate, strontium silicate, metal tungstate, magnesium, silica, zeolite, glass, barium sulfate, calcined calcium sulfate (calcined gypsum), calcium phosphate, fluoroapatite, hydroxyapatite, ceramic powder, metallic soap (zinc myristate, calcium palmitate, aluminum stearate, etc.), and graphite boron nitride; organic powders such as PMMA, silicone resin powder, nylon powder, silk powder, wool powder, urethane powder, and PTFE; inorganic white pigments such as titanium dioxide, zinc oxide; inorganic red pigments such as iron oxide (rouge) and iron titanate; inorganic brown pigments such as γ-iron oxide; inorganic yellow pigments such as yellow iron oxide and loess; inorganic black pigments such as black iron oxide, carbon black, and low oxidation titanium oxide; inorganic violet pigments such as manganese violet and cobalt violet; inorganic green pigments such as chromium oxide, chromium hydroxide, and cobalt titanate; inorganic blue pigments such as ultramarine and Prussian blue; inorganic pearlescent pigments such as titanium oxide coated mica, titanium oxide coated bismuth oxychloride, titanium oxide coated talc, colored titanium oxide coated mica, bismuth oxychloride, and fish scale flake; metal powder pigments such as aluminum powder and copper powder; organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404; organic lake pigments: zirconium lakes, barium lakes, and aluminum lakes, such as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1.

The preferable average particle diameter for the base powder used in the present invention is 0.1 to 1000 μm.

The acid dye laminate pigment of the present invention can be prepared by allowing the above acid dye/water-swellable clay mineral complex to contact the base powder in water. For example, the pigment powder can be obtained by adding the base powder to a water dispersion of the above acid dye/water-swellable clay mineral complex, uniformly dispersing it, and subsequent solid-liquid separation, as necessary, washing, and drying. For dispersion, ultrasonication may be used. As a water dispersion of the acid dye/water-swellable clay mineral complex, a dispersion before the solid-liquid separation in the preparation of the acid dye/water-swellable clay mineral complex may be used. Alternatively, the acid dye/water-swellable clay mineral complex is isolated once as powder, and the powder may be dispersed again in water. The treatment condition of the acid dye/water-swellable clay mineral complex and the base powder can be appropriately decided depending upon raw materials etc. Mixing is usually conducted for 1 to 24 hours at room temperature.

If the surface charge of the used base powder is the same as that of the acid dye/water-swellable clay mineral complex (usually positive), the surface charge of the basic powder should be reversed by ionic molecules. On this occasion, a polymer electrolyte having one or more ionic functional group can be used as the ionic molecule. The ionic molecules are classified into polyacid and polybase depending upon the kind of the ionic functional group.

A polyacid ionizes to a polyanion by releasing protons. The examples of polyacids include polyphosphoric acid, polyvinyl or polystyrene sulfuric acid, polyvinyl or polystyrene sulfonic acid, and polyvinyl carboxylic acid. The examples of their salts include polyphosphate, polysulfate, polysulfonate, polyacrylate, and polycarbonate.

The examples of polybases include polyamines such as polyethylene amine, polyvinyl amine, and polyvinyl pyridine; and polyammonium salts such as poly(diallyldimethylammonium chloride).

These polymer electrolytes can be used to reverse the charge of the surface when two or more layer of the acid dye/water-swellable clay mineral complex is laminated.

These polymer electrolytes are used in water dispersion of an appropriate concentration. Specifically, powder to be treated (base powder or acid dye laminate pigment) with the opposite surface charge is added to an aqueous solution of a polymer electrolyte, and the polymer electrolyte is electrostatically adsorbed on the surface of the powder to be treated.

The surface of the acid dye laminate pigment of the present invention can be treated by the heretofore-known method so far as the effect of the present invention is not undermined. For example, when hydrophobicity is necessary, silicone treatment, fluorine-modified alkyl treatment, higher fatty acid, higher alcohol, fatty acid ester, metallic soap, amino acid, alkyl phosphate, cationic surfactant, dextrin fatty acid ester, etc. can be applied. The surface treatment of other types is also possible. The present invention includes acid dye laminate pigments, the surface of which is treated by such methods.

The above acid dye laminate pigment of the present invention is a powder in which clay mineral intercalating acid dye is adsorbed and/or coated on the surface of the base powder. The particle size can be widely varied by changing the particle size of the base powder and the number of laminated layers. In addition, the acid dye laminate pigment of the present invention can be easily separated by solid-liquid separation such as filtration and centrifugal separation. Since the pigment has low aggregation property, it is possible to use the pigment after only simple pulverization. Furthermore, since the acid dye is tightly retained on the base by intercalation between the layers of the clay mineral, dissolution resistance, lightfastness, and chlorine resistance are excellent. Furthermore, the acid dye content can be easily increased by lamination; thus, the coloring ability and coloring property can be improved. It is also possible to prepare pigments with high transparency and high hiding power by changing the particle size and refractive index of the base powder.

In addition to the above-described acid dye laminate pigment, components usually used in cosmetics and pharmaceuticals can be blended in the cosmetics of the present invention so far as the effect of the present invention is not undermined, and the preparation can be carried out by the conventional method. Examples of oil components include silicone oils such as dimethylpolysiloxane, cyclic dimethylpolysiloxane, and methylphenylpolysiloxane; various hydrocarbon oils such as squalane, liquid paraffin, light isoparaffin, vaseline, microcrystalline wax, ozokerite, and ceresin; higher fatty acids such as myristic acid, palmitic acid, stearic acid, oleic acid, isostearic acid, and behenic acid; higher alcohols such as cetyl alcohol, stearyl alcohol, oleyl alcohol, and batyl alcohol; esters such as cetyl 2-ethylhexanoate, 2-ethylhexyl palmitate, 2-octyldodecyl myristate, neopentyl glycol-2-ethylhexanoate, glyceryl trioctanoate, 2-octyldodecyl oleate, isopropyl myristate, myristyl myristate, glyceryl triisostearate, glyceryl trioleate, and glyceryl tricocoate; fats such as olive oil, avocado oil, jojoba oil, sunflower oil, safflower oil, camellia Japonica seed oil, shea butter, macadamia nut oil, mink oil, lanolin, lanolin acetate, lanolin oil, and castor oil; waxes such as Japan wax; fluorinated oils such as perfluoropolyether and perfluorocarbon; silicone resins such as trimethyl siloxysilicate and MDQ resin; and polymers such as polymeric silicone rubber and acrylic-modified silicone copolymer. Other examples include powder components, coloring agent, film forming agent, surfactant, UV absorber, antioxidant, salts, preservative, thickening agent, moisturizer, perfume, water-based components, vitamin, hormone, whitening agent, and antiphlogistic agent.

There is no limitation in the use of the cosmetic of the present invention, and examples include make up cosmetic such as oil-based foundation, emulsion foundation, powdery foundation, dual-use foundation, face powder, blusher, pressed powder, cheek color, lipstick, eye liner, mascara, eye shadow, and nail enamel; and skin care cosmetic such as milky lotion, lotion, cream, sunscreen, and pre-makeup.

The acid dye laminate pigment of the present invention is basically a non-water-soluble powder, and it is used in dispersion in the base as a coloring pigment.

On the other hand, the acid dye/water-swellable clay mineral complex of the present invention can be used as a water-type coloring agent like dye. When the acid dye/water-swellable clay mineral complex of the present invention is added to water, it swells and it is highly dispersed. Thus, a transparent and highly colored aqueous solution can be obtained, and it can be used for a similar application to that of normal acid dye. In addition, the acid dye/water-swellable clay mineral complex of the present invention is excellent in lightfastness and chlorine resistance.

Acid dye has a color-fading problem when in contact with chlorine or light. For example, acid dyes such as Blue No. 1 and Brown No. 201 have extremely poor chlorine resistance, and the color fades by simple addition into tap water. Other acid dyes are also affected by chlorine and light.

The acid dye/water-swellable clay mineral complex of the present invention is excellent in lightfastness and chlorine resistance. In addition, it has a high coloring property and high transparency; thus, it is very useful as a water-type coloring agent.

As colored water-type compositions in which the acid dye/water-swellable clay mineral complex of the present invention can be blended, there are cosmetics containing a water phase, for example, of soluble-type, emulsion-type, or dispersion-type. Specific examples are skin care cosmetics such as skin lotion, wiping lotion, milky lotion, cream, and sunscreen; and make up cosmetics such as foundation, rouge, and cheek color. In addition to cosmetics, it can be used as a water-phase coloring agent without any special limitation. Examples include fragrance products, cold reserving material, toys, sundry articles, and display products. It may also be effective for coloring man-made rivers and lakes in parks and theme parks.

2-2 Water-Soluble Dye/Water-Swellable Clay Mineral Complex

In the water-soluble dye/water-swellable clay mineral complex of the present invention, a nonionic hydrophilic polymer and water-soluble dye are intercalated between the layers of a water-swellable clay mineral.

In the water-soluble dye/water-swellable clay mineral complex of the present invention, the water-soluble dye can be easily intercalated between the layers of the water-swellable clay mineral by intercalating a nonionic hydrophilic polymer between the layers of the water-swellable clay mineral. Since the interlayer hydrophilicity of the water-swellable clay mineral becomes strong owing to the existence of the nonionic hydrophilic polymer, the water-soluble dye may coadsorb to the water-swellable clay mineral. The intercalated water-soluble dye does not easily desorb by washing.

In the water-soluble dye/water-swellable clay mineral complex of the present invention, water-soluble dye other than acid dye, for example, water-soluble basic dye can also be used.

Examples of a nonionic hydrophilic polymer used in the water-soluble dye/water-swellable clay mineral complex of the present invention include synthetic polymers such as poly (vinyl pyrrolidone), poly(vinyl alcohol), poly(vinylmethyl ether), poly(ethylene oxide), and ethylene oxide-propylene oxide block copolymer; and polysaccharides such as cellulose and its derivatives, and starch and its derivatives. Among them, poly(vinyl pyrrolidone) and poly(vinyl alcohol) are preferably used.

These nonionic hydrophilic polymers have various molecular weights. In the present invention, there is no special limitation for the molecular weight so far as a water-soluble dye can be contained in the clay mineral. However, if the molecular weight of a nonionic hydrophilic polymer is large, the water-swellable clay mineral tends to flocculate when the nonionic hydrophilic polymer is intercalated between the layers of the water-swellable clay mineral. Therefore, the average molecular weight should preferably be one million or less, more preferably the average molecular weight should be 100 thousands or less.

When a nonionic hydrophilic polymer is intercalated in the water-swellable clay mineral, an aqueous solution of the nonionic hydrophilic polymer is usually used at an appropriate concentration.

As the water-soluble dye usable in the water-soluble dye/water-swellable clay mineral complex of the present invention, any dye can be used so far as it is intercalatable between the layers by coadsorption with the nonionic hydrophilic polymer. Specific examples include the following acid dyes: Red No. 2, Red No. 3, Red No. 102, Red No. 104-1, Red No. 105-1, Red No. 106, Yellow No. 4, Yellow No. 5, Green No. 3, Blue No. 1, Blue No. 2, Red No. 227, Red No. 230-1, Orange No. 205, Yellow No. 202-1, Yellow No. 203, Green No. 204, Blue No. 205, Brown No. 201, Red No. 401, Red No. 504, Orange No. 402, Yellow No. 403-1, Yellow No. 406, Yellow No. 407, Green No. 401, Violet No. 401, Black No. 401, etc. In addition, natural acid dyes such as carminic acid and laccaic acid can be used. Examples of the basic dye include Rhodamine B, methylene blue, magenta, auramine, methyl violet, malachite green, Bismarck brown, mauvein, etc.

When a water-soluble dye is intercalated in the water-swellable clay mineral, an aqueous solution of the water-soluble dye is usually used at an appropriate concentration.

For the water-swellable clay mineral used in the water-soluble dye/water-swellable clay mineral complex of the present invention, there is no special limitation. Specific examples are layered silicate minerals of the smectite group, for example, montmorillonite, beidellite, nontronite, saponite, hectorite, etc., and either natural or synthetic mineral can be used. Examples of commercial product include Kunipia, Smecton (Kunimine Industries), Veegum (R. T. Vanderbilt Company), Laponite (by Laporte Industries), and tetrasilicic fluorine mica. In the practice of the present invention, one or more species can be arbitrarily selected from the layered silicates of the smectite group.

The primary particle diameter of the water-swellable clay mineral is preferably 1 μm or less, more preferably 0.5 μm or less.

When nonionic hydrophilic polymer and water-soluble dye are intercalated, clay mineral is used in an aqueous dispersion at the concentration where gelation does not take place.

The water-soluble dye/water-swellable clay mineral complex can be prepared by allowing water-swellable clay mineral, nonionic hydrophilic polymer, and water-soluble dye to contact each other in water. For example, an aqueous suspension is prepared by sufficiently dispersing a water-swellable clay mineral in water at a concentration where gelation does not take place (e.g. 1 to 5 weight %). A nonionic hydrophilic polymer aqueous solution was mixed with this suspension, and then a dye aqueous solution is added and mixed. The powder of the water-soluble dye/water-swellable clay mineral complex can be obtained from the mixed solution after solid-liquid separation (centrifugal separation etc.), as necessary, washing, drying, and pulverizing. It is possible to add dye before nonionic hydrophilic polymer, or to add an aqueous mixed solution of nonionic hydrophilic polymer and water-soluble dye to the aqueous suspension of the water-swellable clay mineral. However, it is preferable to add nonionic hydrophilic polymer to achieve sufficient intercalation before the addition of water-soluble dye. It is also possible to obtain the powder after intercalating the nonionic hydrophilic polymer into the water-swellable clay mineral. Then the obtained powder can be dispersed in water again and mixed with the water-soluble dye.

The mixing condition of nonionic hydrophilic polymer and water-soluble dye to the water-swellable clay mineral can be appropriately decided depending upon raw materials etc. Stirring is usually conducted for 1 to 24 hours at room temperature.

The water-soluble dye/water-swellable clay mineral complex of the present invention can be used as a water-type coloring agent like water-soluble dye. When the water-soluble dye/water-swellable clay mineral complex of the present invention is added to water, it swells and it is highly dispersed. Thus, a transparent and highly colored aqueous solution can be obtained, and it can be used for a similar application to that of water-soluble dye. In addition, the water-soluble dye/water-swellable clay mineral complex of the present invention is excellent in chlorine resistance.

Water-soluble acid dye has a color-fading problem when in contact with chlorine or light. For example, acid dye such as Brown No. 201 has extremely poor chlorine resistance, and the color fades by simple addition into tap water. Other acid dyes are also affected by chlorine and light. In contrast, the water-soluble dye/water-swellable clay mineral complex of the present invention is excellent in chlorine resistance, and the coloring property and clearness are also very good. Thus, it is very useful as a water-type coloring agent. In addition, the improvement in lightfastness can be expected.

As for colored water-type compositions in which the water-soluble dye/water-swellable clay mineral complex of the present invention can be blended, there are cosmetics containing a water phase, for example, of soluble-type, emulsion-type, or dispersion-type. Specific examples are skin care cosmetics such as skin lotion, wiping lotion, milky lotion, cream, and sunscreen; and make up cosmetics such as foundation, rouge, and cheek color. In addition to cosmetics, it can be used as a water-phase coloring agent without any special limitation. Examples include fragrance products, cold reserving material, toys, sundry articles, and display products. It may also be effective for coloring man-made rivers and lakes in parks and theme parks.

The present invention will hereinafter be described with reference to desirable examples. However, the technical scope of the present invention is not limited by these examples. Unless otherwise noted, the blending quantity is expressed in weight percent.

At first, examples of the water-swellable clay mineral laminated powder of the present invention will be described.

1. Water-swellable Clay Mineral Laminated Powder

Preparation of Water-swellable Clay Mineral Laminated Powder

The present inventors have prepared laminated powders by laminating synthetic fluorphlogopite with poly(diallyldimethylammonium chloride) (PDDA) and sodium polystyrene sulfonate (PSS), as polymer electrolytes, and Laponite, as a water-swellable clay mineral, so that the respective surface charges or ionic charges are alternately positive and negative, and the obtained products were evaluated and reviewed.

EXAMPLE 1-1

Laponite/PDDA/Synthetic Fluorphlogopite Laminated Powder

PDDA/synthetic fluorphlogopite laminated powder was prepared by adsorbing PDDA on fluorphlogopite by immersing negatively charged synthetic fluorphlogopite (Topy Industries, average particle diameter: 30 μm) in 1% aqueous solution of a cationic polymer electrolyte, poly(diallyldimethylammonium chloride) (PDDA) (Aldrich, MW: <200000). The obtained laminated powder was sufficiently washed with water after the adsorption of PDDA.

Subsequently, a negatively charged water-swellable clay mineral Laponite XLG (Laporte Industries) was dispersed in water at a concentration where gelation does not take place (<2%). The dispersion was stirred until a clear Laponite aqueous dispersion was obtained.

To the obtained Laponite aqueous dispersion was added the above PDDA/synthetic fluorphlogopite laminate with the weight ratio, Laponite: PDDA/synthetic fluorphlogopite laminate=1:1. The mixture was blended by stirring, and Laponite/PDDA/synthetic fluorphlogopite laminated powder was obtained after filtering, washing, and drying.

EXAMPLE 1-2

Laponite/PDDA/PSS/PDDA/Synthetic Fluorphlogopite Laminated Powder

In the same way as Example 1-1, PDDA was adsorbed on fluorphlogopite. The obtained PDDA/synthetic fluorphlogopite laminated powder was immersed in a 1% aqueous solution of anionic polymer electrolyte, sodium polystyrene sulfonate (PSS) (Aldrich, MW: 70000), to adsorb PSS on the powder surface. PDDA/PSS/PDDA/synthetic fluorphlogopite laminated powder was prepared by repeating the above PDDA adsorption. The obtained laminated powder was washed well after the adsorption of each polymer electrolyte.

To the Laponite aqueous dispersion obtained in the same way as Example 1-1, the above PDDA/PSS/PDDA/synthetic fluorphlogopite laminated powder was added with the weight ratio, Laponite: PDDA/PSS/PDDA/synthetic fluorphlogopite laminated powder=1:1. The mixture was blended by stirring, filtered, washed, and dried to obtain Laponite/PDDA/PSS/PDDA/synthetic fluorphlogopite laminated powder.

The obtained laminated powders in Examples 1-1 and 1-2 were respectively evaluated by the CHN elemental analysis, ζ-potential measurement, and DFM measurement. The following equipment and conditions were used in the analysis and measurement.

CHN elemental analysis: 2400II CHNS/O (Perkin Elmer)
Measurement of ζ-potential: LEZA60 (Otsuka Electronics), mobile phase solvent: 0.1M NaCl aqueous solution
DFM measurement: SPA400/3800N (Seiko Instruments)
Cantilever: DF-20 (Seiko Instruments) (SiN, spring constant: 20N/m)

Figure 2:
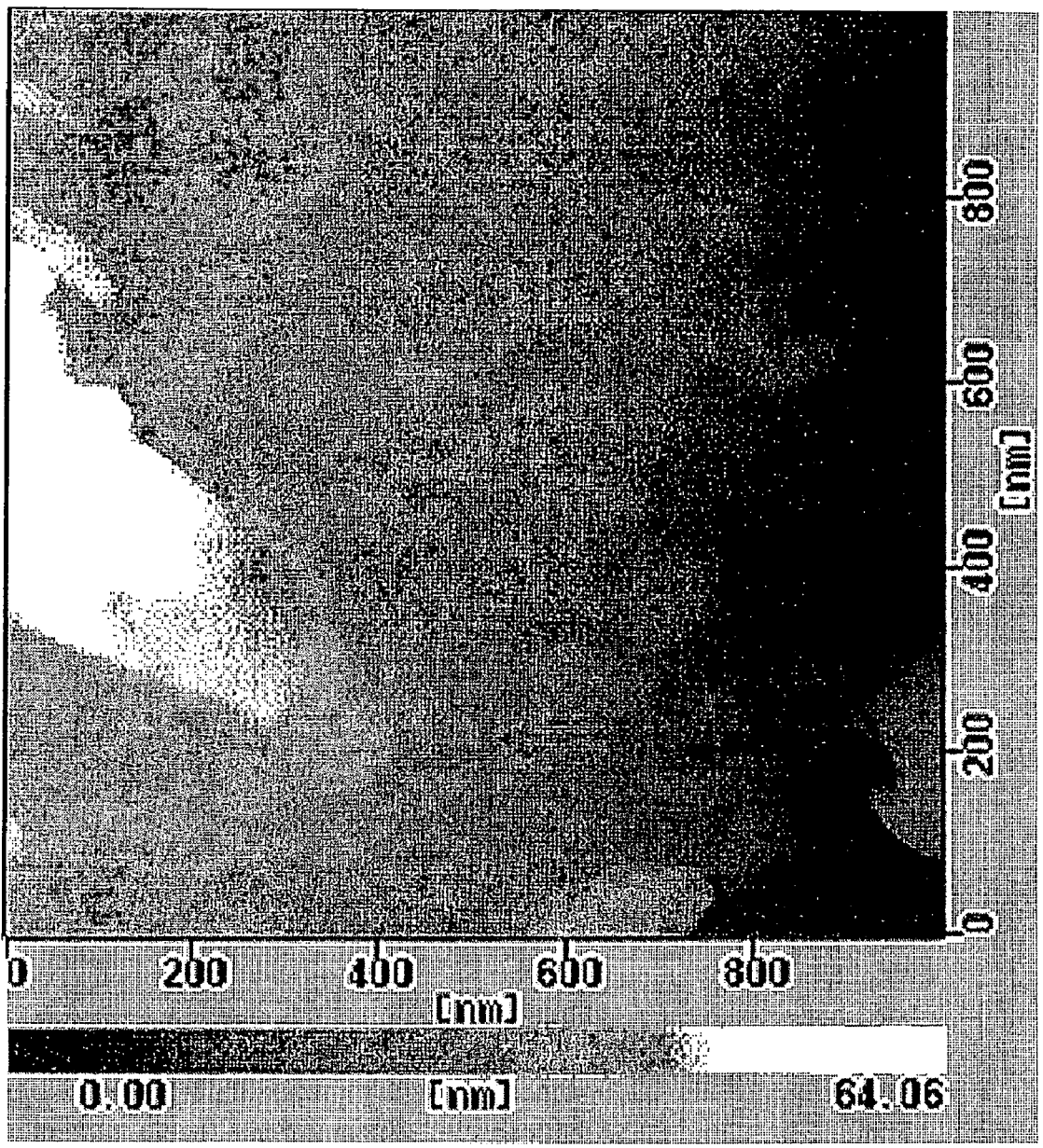
FIG. 2 shows a DFM image of PDDA/synthetic fluorphlogopite.
Figure 3:
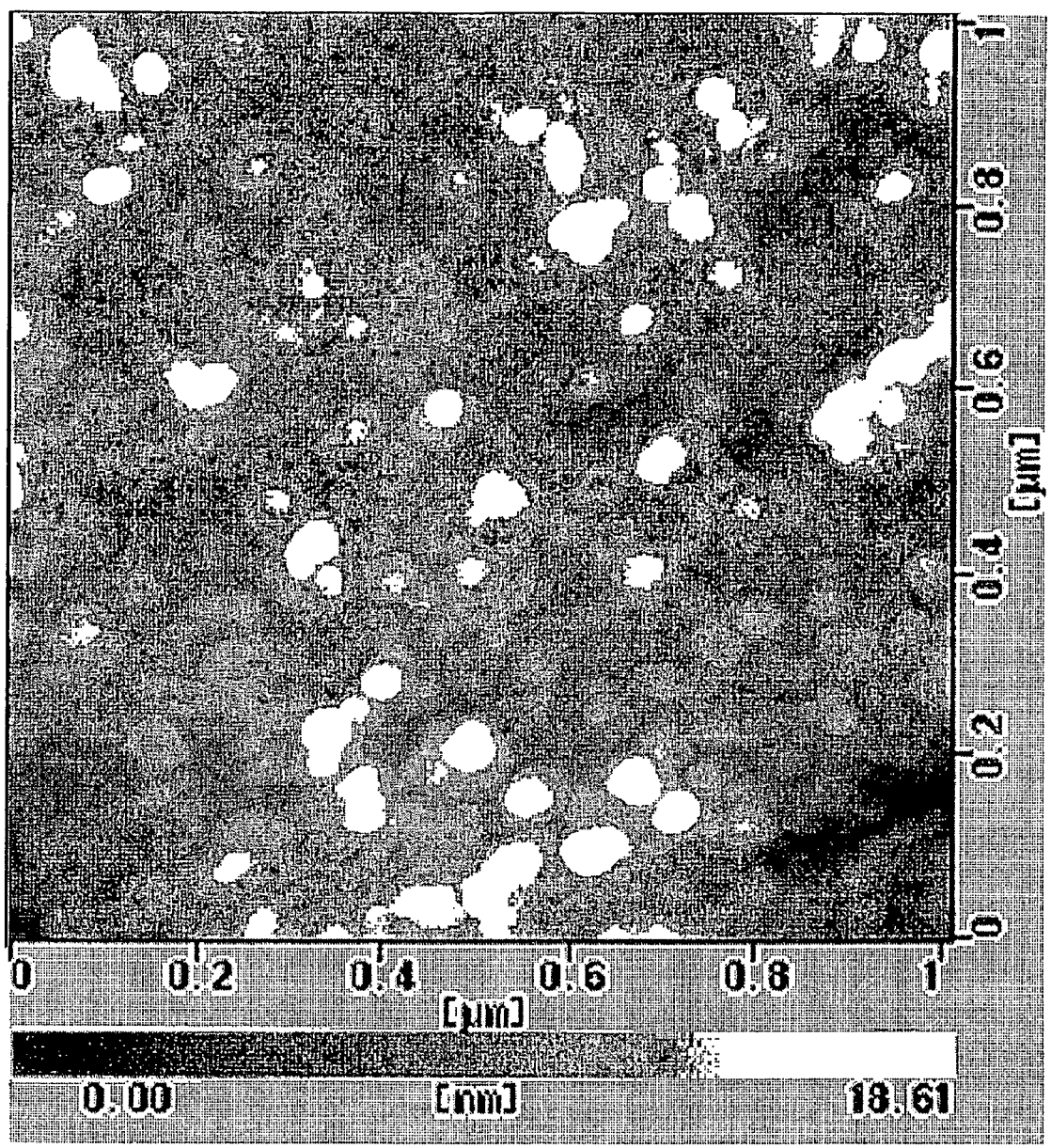
FIG. 3 shows a DFM image of Laponite/PDDA/synthetic fluorphlogopite (Example 1-1), which is one example of the present invention.

The carbon content (% C) obtained by the CHN elemental analysis and the ζ-potential, at each process step, for the laminated powders of Examples 1-1 and 1-2 are shown in Table 1. DFM images, at each process step, for laminated powder of Example 1-1 are shown in FIGS. 1-3.

TABLE 1

| | % C n: 2 | ζ-Potential/mV |
|---|---|---|
| Synthetic fluorphlogopite | 0 | −26.1 |
| PDDA/synthetic fluorphlogopite | 0.40 | +28.2 |
| PSS/PDDA/synthetic fluorphlogopite | 0.78 | −32.2 |
| PDDA/PSS/PDDA/synthetic fluorphlogopite | 1.22 | +30.1 |
| Laponite/PDDA/synthetic fluorphlogopite (Example 1-1) | 0.40 | −13.2 |
| Laponite/PDDA/PSS/PDDA/ synthetic fluorphlogopite (Example 1-2) | 1.21 | −15.2 |

As shown in the results of the CHN elemental analysis (Table 1), the carbon content has increased after the adsorption of PDDA, PSS/PDDA, and PDDA/PSS/PDDA. Thus, it was confirmed that polymer electrolyte was adsorbed in each case. The carbon content after the treatment with Laponite has not changed compared with the carbon content before the treatment. Thus, it was confirmed that desorption of polymer electrolyte has not taken place during the treatment with Laponite.

As shown in the results of the ζ-potential measurement (Table 1), the ζ-potential for the surface of the untreated synthetic fluorphlogopite is ca. −26 mV; thus, the surface is charged negative. On the other hand, since the surface of PDDA/synthetic fluorphlogopite is covered with polycations, the ζ-potential of the surface is ca. +28 mV; thus, the surface is positively charged. The ζ-potential for the surface of Laponite/PDDA/synthetic fluorphlogopite is ca. −13 mV. Thus, it can be confirmed that Laponite with a negative surface potential is laminated. Similarly, the ζ-potential for the surface of Laponite/PDDA/PSS/PDDA/synthetic fluorphlogopite is ca. −15 mV. Thus, it is confirmed that the surface was laminated with Laponite.

As shown in FIGS. 1 to 3, the surface shapes for various powders were observed by the DFM measurement. There was no big difference in shape between the untreated synthetic fluorphlogopite (FIG. 1) and PDDA/synthetic fluorphlogopite (FIG. 2). On the other hand, it was confirmed for Laponite/PDDA/synthetic fluorphlogopite (FIG. 3) that the surface was entirely covered with particles of the size 20 to 40 nm. The roughness height was ca. 5 to 10 nm, indicating that the surface was very uniformly laminated without irregularity. A similar DFM image was also observed for Laponite/PDDA/PSS/PDDA/synthetic fluorphlogopite. Thus, it was confirmed that the surface of the base powder was uniformly covered with water-swellable clay mineral and that a new water-swellable clay mineral laminated powder was prepared.

Adsorption of Cationic Functional Molecule on Laminated Powder

Subsequently, the present inventors tested adsorption of a cationic functional molecule, dimethyldistearylammonium chloride (2C18), on the surface of the laminated powder obtained above, and the product was evaluated and reviewed.

EXAMPLE 1-3

2C18/Laponite/PDDA/synthetic Fluorphlogopite

Laponite/PDDA/synthetic fluorphlogopite of Example 1-1 was added to a 5 mM dimethyldistearylammonium chloride (2C18) aqueous solution warmed at 80° C. (Laponite/PDDA/synthetic fluorphlogopite: 2C18=50:1 (weight ratio)) and mixed by stirring for 1 hour. Then the reactant was washed with 80° C. water, filtered, and dried to obtain 2C18/Laponite/PDDA/synthetic fluorphlogopite.

For the above-obtained laminated powders in Example 1-3, the CHN elemental analysis, water contact angle measurement, and sensory evaluation by panel members for cosmetics were performed; they are for laminated powder itself and powdery foundation thereof. The formulation of the powdery foundation is shown in Table 3, and the evaluation results for the powder itself and as cosmetics thereof are shown in Tables 2 and 4. The details for the sensory evaluation are as follows.

Smoothness and spreadability: The samples were applied to 20 female panel members, and smoothness and spreadability were evaluated.

⊚ More than 16 persons answered "good".
○ 12 to 16 persons
Δ 9 to 11 persons
× 5 to 8 persons
×× Less than 5 persons Endurance of Cosmetics: The samples were applied to 20 female panel members, and the endurance of cosmetics was evaluated.

⊚ More than 16 persons answered "good".
○ 12 to 16 persons
Δ 9 to 11 persons
× 5 to 8 persons
×× Less than 5 persons Evaluation of Powder Itself

TABLE 2

|  | % C | Water contact angle | Smoothness/ Spreadability |
|---|---|---|---|
| Synthetic Fluorphlogopite | 0% | non-measurable (<5°) | Δ |
| Laponite/PDDA/ synthetic fluorphlogopite (Example 1-1) | 0.4% | non-measurable (<5°) | Δ |
| 2C18/Laponite/PDDA/ synthetic fluorphlogopite (Example 1-3) | 1.44% | 55.3° | ⊚ |

TABLE 3

Powdery Foundation

|  | Formulation Example 1-1 | Comparative Example 1-1 |
|---|---|---|
| 2C18/Laponite/PDDA/ synthetic fluorphlogopite | 40 | — |
| Synthetic fluorphlogopite | — | 40 |
| Talc | to 100 | to 100 |
| Titanium dioxide | 10.5 | 10.5 |
| Fine titanium dioxide | 5 | 5 |
| Iron oxide red | 0.8 | 0.8 |
| Iron oxide yellow | 2 | 2 |
| Iron oxide black | 0.1 | 0.1 |
| Spherical nylon powder | 3 | 3 |
| Spherical PMMA powder | 5 | 5 |
| Liquid paraffin | 4 | 4 |
| Vaseline | 4 | 4 |
| Sorbitan sesquiisostearate | 0.8 | 0.8 |
| Paraben | q.s. | q.s. |
| Antioxidant | q.s. | q.s. |
| Perfume | q.s. | q.s. |

Preparation

Powder components and oil components in the formulation were mixed in a Henschel mixer, pulverized twice with a pulverizer, packed in a container (medium resin plate), and molded with a dry press according to a known method.

Evaluation of Blended Cosmetics

TABLE 4

|  | Smoothness/ spreadability | Endurance of cosmetics |
|---|---|---|
| Formulation Example 1-1 | ⊚ | ○ |
| Comparative Example 1-1 | Δ | Δ |

As shown in Table 2, after the surface treatment with 2C18, the carbon content (C %), which is obtained by CHN elemental analysis, has increased ca. 1%. The measurement of the water contact angle shows that the powder surface is hydrophilic before the surface treatment, but it is water-repellent after the surface treatment with 2C18.

Thus, it was confirmed that dimethyldistearyammonium, which is a cationic functional molecule, was adsorbed on the surface with a negative charge and cation exchange sites because the surface is uniformly covered with Laponite. In the evaluation of the powder itself, it was found by the panel members for cosmetics that the smooth feeling and smoothness were improved after the treatment with 2C18. As shown in Table 4, in the evaluation of powdery foundation, smooth feeling and smoothness have improved in Formulation Example 1-1 than comparative Formulation Example 1-1. In addition, the endurance of cosmetics, which is considered to be due to water-repelling property of the surface, has also improved.

Water-swellable Clay Mineral Intercalated with Water-soluble Polymer and Polyhydric Alcohol The present inventors have prepared water-swellable clay mineral intercalated with a water-soluble polymer, poly(vinyl pyrrolidone) (PVP) or a polyhydric alcohol, glycerin, as a functional molecule. With the obtained water-swellable clay mineral, laminated powder was prepared in the same way as the above-described example, and the product was evaluated and reviewed.

PVP/Laponite Complex Powder

Laponite XLG (Laporte Industries), which is a water-swellable clay mineral, was dispersed in water at a concentration where gelation does not take place (<2%), and it was mixed by stirring until a clear Laponite aqueous dispersion is obtained. To this dispersion was added a 5% aqueous solution of poly(vinyl pyrrolidone) (TCI, molecular weight: 10000), which is a water-soluble polymer, with the weight ratio, Laponite:PVP=1:2. The mixture was stirred for 30 minutes, centrifuged, washed, dried at room temperature to obtain PVP/Laponite complex.

Glycerin/Laponite Complex Powder

Glycerin/Laponite complex was prepared in the same way as the above PVP/Laponite complex powder using a polyhydric alcohol, glycerin.

The XRD measurement was performed for the obtained PVP/Laponite complex powder and glycerin/Laponite complex powder to confirm whether PVP or glycerin is intercalated between the layers of Laponite or not.

XRD Measurement

In the XRD measurement of Laponite XLG, a diffraction peak due to (001) of Laponite was observed at 14.5 Å. On the other hand, in the XRD measurement of PVP/Laponite, a peak due to (001) was observed at 29.0 Å. Thus, it was confirmed that the interplanar distance of the basic planes of Laponite was stretched by ca. 14.5 Å, and that PVP was intercalated between the layers of Laponite. Similarly, it was confirmed that the interplanar distance of the basic planes of glycerin/Laponite was stretched by ca. 4.0 Å, and that glycerin was intercalated between the layers of Laponite.

EXAMPLE 1-4

(PVP/Laponite)/PDDA/Muscovite

Muscovite was used as a base powder. Muscovite was added, in the same way as Example 1-1, to a 10% PDDA aqueous solution with the weight ratio, PDDA:muscovite=10:1. The mixture was blended by stirring, filtered, and washed to obtain PDDA/muscovite. The carbon content (% C) of the obtained muscovite was 0.45% by the CHN elemental analysis, and the ζ-potential was +38 mV. Thus, it was confirmed that a sufficient amount of PDDA was adsorbed on the surface of muscovite. This PDDA/muscovite was added to an aqueous dispersion of the above PVP/Laponite complex powder at a concentration where gelation does not take place. The mixture was blended by stirring, filtered, and washed to obtain (PVP/Laponite)/PDDA/muscovite.

EXAMPLE 1-5

(Glycerin/Laponite)/PDDA/Muscovite (Glycerin/Laponite)/PDDA/muscovite was obtained, in the same way as Example 1-4, from the above glycerin/Laponite complex powder.

The sensory evaluation for the obtained (PVP/Laponite)/PDDA/muscovite and (glycerin/Laponite)/PDDA/muscovite complexes was conducted by panel members for cosmetics using powdery foundations containing the complexes. The formulation is shown in Table 5, and the evaluation results are shown in Table 6. Details for the sensory evaluation are as follows.

Moist feeling and Smoothness: The samples were applied to 20 female panel members, and the moist feeling and smoothness were evaluated.

⊚ More than 16 persons answered "good".
○ 12 to 16 persons
Δ 9 to 11 persons
× 5 to 8 persons
×× Less than 5 persons

TABLE 5

|  | Formulation Example 1-2 | Formulation Example 1-3 | Comparative Example 1-2 |
|---|---|---|---|
| (PVP/Laponite)/PDDA/muscovite | 40 | — | — |
| (Glycerin/Laponite)/PDDA/muscovite | — | 40 | — |
| Muscovite | — | — | 40 |
| Talc | to 100 | to 100 | to 100 |
| Titanium dioxide | 10.5 | 10.5 | 10.5 |
| Fine titanium dioxide | 5 | 5 | 5 |
| Iron oxide red | 0.8 | 0.8 | 0.8 |
| Iron oxide yellow | 2 | 2 | 2 |
| Iron oxide black | 0.1 | 0.1 | 0.1 |
| Spherical nylon powder | 3 | 3 | 3 |
| Spherical silicone powder | 5 | 5 | 5 |
| Liquid paraffin | 4 | 4 | 4 |
| Dimethicone | 4 | 4 | 4 |
| Sorbitan sesquiisostearate | 0.8 | 0.8 | 0.8 |
| Paraben | q.s. | q.s. | q.s. |
| Antioxidant | q.s. | q.s. | q.s. |
| Perfume | q.s. | q.s. | q.s. |

Preparation

Powder components and oil components in the formulation were mixed in a Henschel mixer, pulverized twice with a pulverizer, packed in a container (medium resin plate), and molded with a dry press according to a known method.

TABLE 6

|  | Moist feeling/Smoothness |
|---|---|
| Formulation Example 1-2 | ○ |
| Formulation Example 1-3 | ○ |
| Comparative Example 1-2 | X |

From the above results, it was found that moist feeling and the smooth feeling can be imparted to cosmetics when the following component is blended into cosmetics. The component was obtained by intercalating water-soluble polymer and polyhydric alcohol, in advance, between the layers of the water-swellable clay mineral and laminating it on base powder.

Dye/Water-swellable Clay Mineral Complex and Dye/Water-soluble Polymer/Water-swellable Clay Mineral Complex The present inventors prepared water-swellable clay mineral complexes containing dye and water-swellable clay mineral complexes containing intercalated water-soluble polymer and coadsorbed dye. In the same way as the above-mentioned examples, laminated powders were prepared using these complexes, and the products were evaluated and reviewed.

Dye/Water-swellable Clay Mineral Complex Powder

Sudan III/Laponite Complex Powder

To a 10 ml toluene solution of Sudan III (0.2%) was added 3 g of a water-swellable clay mineral, Laponite XLG (Laporte Industries). The mixture was blended by stirring, centrifuged, and dried under reduced pressure to obtain Sudan III/Laponite complex. The obtained powder was red.

Violamine R/Laponite Complex Powder

To a 20 ml ethanol solution of violamine R (0.05%) was added 3 g of Laponite XLG (Laporte Industries). The mixture was blended by stirring, centrifuged, and dried under reduced pressure to obtain violamine R Laponite complex. The obtained powder was red.

Alizurine Purple/Laponite Complex Powder

To a 10 ml ethanol solution of Alizurine Purple (0.07%) was added 3 g of Laponite XLG (Laporte Industries). The mixture was blended by stirring, centrifuged, and dried under reduced pressure to obtain Alizurine Purple/Laponite complex. The obtained powder was blue-violet.

Chlorophyll a/Laponite Complex Powder

To a 10 ml toluene solution of chlorophyll a (2%) was added 3 g of Laponite XLG (Laporte Industries). The mixture was blended by stirring, centrifuged, and dried under reduced pressure to obtain chlorophyll a/Laponite complex. The obtained powder was green.

Dye/Water-soluble Polymer/Water-swellable Clay Mineral Complex Powder

Violamine R/PVP/Laponite Complex Powder

To a 20 ml ethanol solution of violamine R (0.05%) was added 3 g of the above PVP/Laponite. The mixture was blended by stirring, centrifuged, and dried under reduced pressure to obtain violamine R/PVP/Laponite complex. The obtained powder was red.

Lipophilic dyes, Sudan III and Alizurine Purple were not adsorbed when the host was PVP/Laponite. Therefore, it is suggested that water-soluble violamine R is coadsorbed to the PVP layer, which is a water-soluble polymer.

EXAMPLE 1-6

((Sudan III/Laponite)/PDDA)$_5$/Synthetic Fluorphlogopite

Synthetic fluorphlogopite was used as a base powder. Synthetic fluorphlogopite was added, in the same way as Example 1-1, to a 5% PDDA aqueous solution with the weight ratio, PDDA:synthetic fluorphlogopite=1:1. The mixture was blended by stirring, filtered, and washed to obtain PDDA/synthetic fluorphlogopite. This PDDA/synthetic fluorphlogopite was added to an aqueous dispersion of the above Sudan III/Laponite complex powder at a concentration where gelation does not take place. The mixture was blended by stirring, filtered, and washed to obtain (Sudan III/Laponite)/PDDA/synthetic fluorphlogopite. In addition, a series of steps from the above PDDA coating process were repeated five times to obtain the five-layered structure, ((Sudan III/Laponite)/PDDA)$_5$/synthetic fluorphlogopite.

EXAMPLE 1-7

((Alizurine Purple/Laponite)/PDDA)$_5$/Synthetic Fluorphlogopite ((Alizurine Purple/Laponite)/PDDA)$_5$/synthetic fluorphlogopite was obtained, in the same way as Example 1-6, using the above Alizurine Purple/Laponite complex powder.

EXAMPLE 1-8

((Chlorophyll a/Laponite)/PDDA)$_5$/Synthetic Fluorphlogopite ((Chlorophyll a/Laponite)/PDDA)$_5$/synthetic fluorphlogopite was obtained, in the same way as Example 1-6, using the above chlorophyll a/Laponite complex powder.

EXAMPLE 1-9

((Violamine R/Laponite)/PDDA)$_5$/Synthetic Fluorphlogopite ((Violamine R/Laponite)/PDDA)$_5$/synthetic fluorphlogopite was obtained, in the same way as Example 1-6, using the above violamine R/Laponite complex powder.

EXAMPLE 1-10

((Violamine R/PVP/Laponite)/PDDA)$_5$/synthetic fluorphlogopite ((Violamine R/PVP/Laponite)/PDDA)$_5$/synthetic fluorphlogopite was obtained, in the same way as Example 1-6, using the above violamine R/PVP/Laponite complex powder.

The sensory evaluation for the obtained ((Chlorophyll a/Laponite)/PDDA)$_5$/synthetic fluorphlogopite (Example 1-8), ((Violamine R/Laponite)/PDDA)$_5$/synthetic fluorphlogopite (Example 1-9) and ((Violamine R/PVP/Laponite)/PDDA)$_5$/synthetic fluorphlogopite (Example 1-10) was conducted by panel members for cosmetics using powdery foundations containing the powders. The formulation is shown in Table 7, and the evaluation results are shown in Table 8. Details for the sensory evaluation are as follows.

Clearness and Brightness: The samples were applied to 20 female panel members, and clearness and brightness of the finish were evaluated.

◎ More than 16 persons answered "good".
○ 12 to 16 persons
Δ 9 to 11 persons
× 5 to 8 persons
×× Less than 5 persons

TABLE 7

|  | Formulation Example | | | Comparative Example 1-3 |
|---|---|---|---|---|
|  | 1-4 | 1-5 | 1-6 |  |
| ((Violamine R/Laponite)/PDDA)$_5$/ synthetic fluorphlogopite complex | 30 | — | — | — |
| ((Chlorophyll a/Laponite)/PDDA)$_5$/ synthetic fluorphlogopite complex | — | 30 | — | — |
| ((Violamine R/PVP/Laponite)/ PDDA)$_5$/synthetic fluorphlogopite complex | — | — | 30 | — |
| Synthetic fluorphlogopite | — | — | — | 30 |
| Talc | to 100 | to 100 | to 100 | to 100 |
| Titanium dioxide | 10.5 | 10.5 | 10.5 | 10.5 |
| Fine titanium dioxide | 5 | 5 | 5 | 5 |
| Iron oxide red | 0.8 | 0.8 | 0.8 | 0.8 |
| Iron oxide yellow | 2 | 2 | 2 | 2 |
| Iron oxide black | 0.1 | 0.1 | 0.1 | 0.1 |
| Spherical nylon powder | 3 | 3 | 3 | 3 |
| Spherical silicone powder | 5 | 5 | 5 | 5 |
| Liquid paraffin | 4 | 4 | 4 | 4 |
| Dimethicone | 4 | 4 | 4 | 4 |
| Sorbitan sesquiisostearate | 0.8 | 0.8 | 0.8 | 0.8 |
| Paraben | q.s. | q.s. | q.s. | q.s. |
| Antioxidant | q.s. | q.s. | q.s. | q.s. |
| Perfume | q.s. | q.s. | q.s. | q.s. |

Preparation

Powder components and oil components in the formulation were mixed in a Henschel mixer, pulverized twice with a pulverizer, packed in a container (medium resin plate), and molded with a dry press according to a known method.

TABLE 8

|  | Clearness and Brightness |
|---|---|
| Formulation Example 1-4 | ○ |
| Formulation Example 1-5 | ○ |
| Formulation Example 1-6 | ○ |
| Comparative Example 1-3 | X |

From the above results, it was found that the color of powder can be easily adjusted by laminated powder which is laminated, on the base powder, a complex powder of water-swellable clay mineral and organic dye or a complex powder of water-swellable clay mineral containing intercalated water-soluble polymer and coadsorbed organic dye. It was also found that the laminated powder can impart excellent clearness and brightness on finishing of cosmetics when the laminated powder is blended in the cosmetics.

FORMULATION EXAMPLE 1-7

Dual-use Foundation

| | |
|---|---|
| (1) Silicone-treated talc | To 100 |
| (2) Silicone-treated sericite | 20.0 |
| (3) Silicone-treated mica | 10.0 |
| (4) Silicone-treated titanium oxide | 10.0 |
| (5) Silicone-treated red iron oxide | 0.8 |
| (6) Silicone-treated yellow iron oxide | 3.0 |
| (7) Silicone-treated black iron oxide | 0.2 |
| (8) (Glycerin/Laponite)/PDDA/muscovite | 10.0 |
| (9) Liquid paraffin | 4.0 |
| (10) Vaseline | 4.0 |
| (11) Sorbitan sesquiisostearate | 0.8 |
| (12) Preservative | q.s. |
| (13) Antioxidant | q.s. |
| (14) Perfume | q.s. |

Preparation

Powder components and oil components in the formulation were mixed in a Henschel mixer, pulverized twice with a pulverizer, packed in a container (medium resin plate), and molded with a dry press according to a known method.

FORMULATION EXAMPLE 1-8

Dual-use Foundation

| | |
|---|---|
| (1) Silicone-treated talc | to 100 |
| (2) Silicone-treated sericite | 20.0 |
| (3) Silicone-treated mica | 10.0 |
| (4) Silicone-treated titanium oxide | 10.0 |
| (5) Silicone-treated red iron oxide | 0.8 |
| (6) Silicone-treated yellow iron oxide | 3.0 |
| (7) Silicone-treated black iron oxide | 0.2 |
| (8) (PVP/Laponite)/PDDA/muscovite | 10.0 |
| (9) Liquid paraffin | 4.0 |
| (10) Vaseline | 4.0 |
| (11) Sorbitan sesquiisostearate | 0.8 |
| (12) Preservative | q.s. |
| (13) Antioxidant | q.s. |
| (14) Perfume | q.s. |

Preparation

This was prepared in a similar way to Formulation Example 1-7.

FORMULATION EXAMPLE 1-9

Dual-use Foundation

| | |
|---|---|
| (1) Silicone-treated talc | to 100 |
| (2) Silicone-treated sericite | 20.0 |
| (3) Silicone-treated mica | 10.0 |
| (4) Silicone-treated titanium oxide | 10.0 |
| (5) Silicone-treated red iron oxide | 0.8 |
| (6) Silicone-treated yellow iron oxide | 3.0 |
| (7) Silicone-treated black iron oxide | 0.2 |
| (8) 2C18/Laponite/PDDA/synthetic fluorphlogopite | 20.0 |
| (9) Liquid paraffin | 4.0 |
| (10) Vaseline | 4.0 |
| (11) Sorbitan sesquiisostearate | 0.8 |
| (12) Preservative | q.s. |
| (13) Antioxidant | q.s. |
| (14) Perfume | q.s. |

Preparation

This was prepared in a similar way to Formulation Example 1-7.

FORMULATION EXAMPLE 1-10

Dual-use Foundation

| | |
|---|---|
| (1) Silicone-treated talc | to 100 |
| (2) Silicone-treated sericite | 20.0 |
| (3) Silicone-treated titanium oxide | 10.0 |
| (4) Silicone-treated red iron oxide | 0.8 |
| (5) Silicone-treated yellow iron oxide | 3.0 |
| (6) Silicone-treated black iron oxide | 0.2 |
| (7) (Violamine R/Laponite)/PDDA/synthetic fluorphlogopite | 30.0 |
| (8) Liquid paraffin | 4.0 |
| (9) Vaseline | 4.0 |
| (10) Sorbitan sesquiisostearate | 0.8 |
| (11) Preservative | q.s. |
| (12) Antioxidant | q.s. |
| (13) Perfume | q.s. |

Preparation

This was prepared in a similar way to Formulation Example 1-7.

FORMULATION EXAMPLE 1-11

Face Powder

| | |
|---|---|
| (1) Mica | 10.0 |
| (2) Talc | to 100 |
| (3) Zinc oxide | 5.0 |
| (4) Fine titanium oxide | 3.0 |
| (5) 2C18/Laponite/PDDA/synthetic fluorphlogopite | 10.0 |
| (6) Vaseline | 1.0 |
| (7) Squalane | 2.0 |
| (8) Ester oil | 1.0 |
| (9) Preservative | q.s. |
| (10) Antioxidant | q.s. |
| (11) Perfume | q.s. |

Preparation

Powder components and oil components in the formulation were mixed in a Henschel mixer, pulverized twice with a pulverizer, packed in a container (medium resin plate), and molded with a dry press according to a known method.

FORMULATION EXAMPLE 1-12

Face Powder

| | |
|---|---|
| (1) Mica | 10.0 |
| (2) Talc | to 100 |

-continued

| | |
|---|---|
| (3) Zinc oxide | 5.0 |
| (4) Fine titanium oxide | 3.0 |
| (5) (PVP/Laponite)/PDDA/muscovite | 10.0 |
| (6) Vaseline | 1.0 |
| (7) Squalane | 2.0 |
| (8) Ester oil | 1.0 |
| (9) Preservative | q.s. |
| (10) Antioxidant | q.s. |
| (11) Perfume | q.s. |

Preparation

This was prepared in a similar way to Formulation Example 1-11.

FORMULATION EXAMPLE 1-13

Face Powder

| | |
|---|---|
| (1) Mica | 10.0 |
| (2) Talc | to 100 |
| (3) Zinc oxide | 5.0 |
| (4) Fine titanium oxide | 3.0 |
| (5) (Violamine R/Laponite)/PDDA/synthetic fluorphlogopite | 10.0 |
| (6) Vaseline | 1.0 |
| (7) Squalane | 2.0 |
| (8) Ester oil | 1.0 |
| (9) Preservative | q.s. |
| (10) Antioxidant | q.s. |
| (11) Perfume | q.s. |

Preparation

This was prepared in a similar way to Formulation Example 1-11.

FORMULATION EXAMPLE 1-14

Face Powder

| | |
|---|---|
| (1) Mica | 10.0 |
| (2) Talc | to 100 |
| (3) Zinc oxide | 5.0 |
| (4) Fine titanium oxide | 3.0 |
| (5) (Glycerin/Laponite)/PDDA/PMMA | 10.0 |
| (6) Vaseline | 1.0 |
| (7) Squalane | 2.0 |
| (8) Ester oil | 1.0 |
| (9) Preservative | q.s. |
| (10) Antioxidant | q.s. |
| (11) Perfume | q.s. |

Preparation

This was prepared in a similar way to Formulation Example 1-11.

FORMULATION EXAMPLE 1-15

Pre-makeup Lotion

| Oil phase | |
|---|---|
| (1) Decamethyl cyclopenta siloxane | to 100 |
| (2) Polyether-modified silicone | 3.0 |
| (3) (Violamine R/PVP/Laponite)/PDDA/synthetic fluorphlogopite (silicone-treated) | 10.0 |
| (4) Trimethyl siloxysilicate | 2.0 |
| Water phase | |
| (5) 1,3-Butylene glycol | 5.0 |
| (6) Dynamite glycerin | 2.0 |
| (7) Preservative | 0.5 |
| (8) Purified water | 30.0 |

Preparation

To the oil phase heated to 70° C. was added the water phase, and the mixture was sufficiently emulsified with an emulsifying machine. Then the emulsion was cooled with stirring, poured into a container at less than 35° C., and allowed to cool to obtain the desired pre-makeup lotion.

FORMULATION EXAMPLE 1-16

Pre-makeup Lotion

| Oil phase | |
|---|---|
| (1) Decamethyl cyclopenta siloxane | to 100 |
| (2) Polyether-modified silicone | 3.0 |
| (3) (Glycerin/Laponite)/synthetic fluorphlogopite (silicone-treated) | 10.0 |
| (4) Trimethyl siloxysilicate | 2.0 |
| Water phase | |
| (5) 1,3-Butylene glycol | 5.0 |
| (6) Dynamite glycerin | 2.0 |
| (7) Preservative | 0.5 |
| (8) Purified water | 30.0 |

Preparation

This was prepared in a similar way to Formulation Example 1-15.

FORMULATION EXAMPLE 1-17

Eye Shadow

| | |
|---|---|
| (1) Talc | to 100 |
| (2) Sericite | 7.0 |
| (3) Mica | 15.0 |
| (4) Spherical PMMA powder | 3.0 |
| (5) (PVP/Laponite)/PDDA/muscovite | 10.0 |
| (6) Barium sulfate | 4.0 |
| (7) Iron oxide | 1.5 |
| (8) Squalane | 2.0 |
| (9) Dimethylpolysiloxane | 2.0 |
| (10) Sorbitan monooleate | 0.5 |
| (11) Preservative | q.s. |
| (12) Perfume | q.s. |

Preparation

Powder components and oil components in the formulation were mixed in a Henschel mixer, pulverized twice with a pulverizer, packed in a container (medium resin plate), and molded with a dry press according to a known method.

FORMULATION EXAMPLE 1-18

Oil Stick

| | |
|---|---|
| (1) Carnauba wax | 1.0 |
| (2) Candelilla wax | 2.0 |
| (3) Ceresin | 10.0 |
| (4) Squalane | to 100 |
| (5) Glyceryl triisooctanoate | 9.0 |
| (6) Glyceryl diisostearate | 13.0 |
| (7) Dimethylpolysiloxane (viscosity: 90,000 mPa·s at 25° C.) | 5.0 |
| (8) Dimethylpolysiloxane (viscosity: 1,000 mPa·s at 25° C.) | 5.0 |
| (9) Silicone resin | 8.0 |
| (10) Hydroxypropyl-β-cyclodextrin | 1.0 |
| (11) Cholesteryl macadamiate | 3.5 |
| (12) Synthetic sodium magnesium silicate | 0.5 |
| (13) Hydrophobic silica | 0.5 |
| (14) Purified water | 2.0 |
| (15) Spherical silicone resin powder coated mica | 3.0 |
| (16) 2C18/Laponite/PDDA/synthetic fluorphlogopite | 5.0 |
| (17) Barium sulfate | 3.0 |
| (18) Coloring material | q.s. |
| (19) Preservative | q.s. |
| (20) Perfume | q.s. |

Preparation

Components 12 to 13 were dispersed in component 11, which had been heated to 60° C., and to the mixture was added uniformly dissolved components 10 and 14 and stirred well. The above mixture was added to components 1 to 9, which had been dissolved under heating, and stirred well. Then components 15 to 20 were added to the mixture and dispersed; the product was filled into a container to obtain an oil stick.

FORMULATION EXAMPLE 1-19

Cream

| | |
|---|---|
| Oil phase | |
| (1) Decamethyl cyclopenta siloxane | 10.5 |
| (2) Dimethylpolysiloxane (6 CS/25° C.) | 4.0 |
| (3) Stearyl alcohol | 1.5 |
| (4) Vaseline | 5.0 |
| (5) Squalane | 1.0 |
| (6) Vitamin E acetate | 0.01 |
| (7) (Glycerin/Laponite)/PDDA/muscovite | 5.0 |
| (8) Polyether-modified silicone | 2.0 |
| Water phase | |
| (9) Preservative | 0.2 |
| (10) 1,3-Butylene glycol | 17.0 |
| (11) Purified water | to 100 |

Preparation

Powder components were added to the oil phase, which had been heated to 70° C. and had been stirred. Then the mixture was dispersed with a homomixer at 70° C. and cooled to room temperature. To this was added the water phase, and the mixture was emulsified with the homomixer to obtain the cream.

FORMULATION EXAMPLE 1-20

Sunscreen Lotion

| | |
|---|---|
| Oil phase | |
| (1) Dimethylpolysiloxane (6 CS/25° C.) | 5.0 |
| (2) Dimethylpolysiloxane (1.5 CS/25° C.) | 13.0 |
| (3) Phenyl-modified methylphenylpolysiloxane | 3.0 |
| (4) ((Violamine R/Laponite)/PDDA)$_5$/titanium dioxide coated mica (red interference color) | 5.0 |
| (5) Polyether-modified silicone | 2.0 |
| Water phase | |
| (6) Sodium chloride | 9.0 |
| (7) Perfume | 0.2 |
| (8) Preservative | 0.2 |
| (9) Ethanol | 5.0 |
| (10) Purified water | to 100 |

Preparation

Powder components were added to the oil phase, which had been heated to 70° C. and had been stirred. Then the mixture was dispersed with a homomixer at 70° C. and cooled to room temperature. To this was added the water phase, and the mixture was emulsified with the homomixer to obtain the sunscreen lotion.

FORMULATION EXAMPLE 1-21

Liquid Emulsion Foundation

| | |
|---|---|
| Oil phase | |
| (1) Decamethyl cyclopenta siloxane | to 100 |
| (2) Trimethyl siloxysilicate | 3.0 |
| (3) Dimethylpolysiloxane | 5.0 |
| (4) Dimethylpolysiloxane polyoxyalkylene copolymer | 2.5 |
| (5) Sorbitan sesquiisostearate | 2.0 |
| Powder components | |
| (6) Silicone-treated talc | 5.0 |
| (7) Silicone-treated titanium dioxide | 5.0 |
| (8) ((Violamine R/PVP/Laponite)/PDDA)$_5$/titanium dioxide | 5.5 |
| (9) Silicone-treated nylon powder | 4.0 |
| (10) Silicone-treated coloring pigment | 2.0 |
| Water phase | |
| (11) 1,3-Butylene glycol | 3.0 |
| (12) Ethanol | 13.0 |
| (13) Purified water | 10.0 |

Preparation

Powder components were added to the oil phase, which had been heated to 70° C. and had been stirred. Then the mixture was dispersed with a homomixer at 70° C. and cooled to room temperature. To this was added the water phase, and the mixture was emulsified with the homomixer to obtain the liquid foundation.

FORMULATION EXAMPLE 1-22

Creamy Emulsion Foundation

| Oil phase | |
|---|---|
| (1) Decamethyl cyclopenta siloxane | to 100 |
| (2) Trimethyl siloxysilicate | 3.0 |
| (3) Dimethylpolysiloxane | 5.0 |
| (4) Sorbitan sesquiisostearate | 2.0 |
| (5) Dimethylpolysiloxane polyoxyalkylene copolymer | 3.5 |
| (6) Dimethylstearylammonium hectorite | 2.0 |
| Powder components | |
| (7) Silicone-treated talc | 5.0 |
| (8) Silicone-treated titanium dioxide | 5.0 |
| (9) ((Chlorophyll a/Laponite)/PDDA)$_5$/synthetic fluorphlogopite | 5.5 |
| (10) Silicone-treated nylon powder | 4.0 |
| (11) Silicone-treated coloring pigment | 2.0 |
| Water phase | |
| (12) 1,3-Butylene glycol | 3.0 |
| (13) Ethanol | 20.0 |
| (14) Purified water | 20.0 |

Preparation

Powder components were added to the oil phase, which had been heated to 70° C. and had been stirred. Then the mixture was dispersed with a homomixer at 70° C. and cooled to room temperature. To this was added the water phase, and the mixture was emulsified with the homomixer to obtain the creamy foundation.

2. Dye/Water-Swellable Clay Mineral Complex

The present inventors have also investigated the complexation method of dye to water-swellable clay mineral in order to improve various tolerances of dye such as dissolution resistance, lightfastness, and chlorine resistance of dye/water-swellable clay mineral complex, in which water-swellable clay mineral and dye are complexed.

2-1 Acid Dye/Water-Swellable Clay Mineral Complex

Preparation of Acid Dye/Polybase/Water-swellable Clay Mineral Complex

EXAMPLE 2-1

An aqueous dispersion of the clay was obtained by adding 5 g of Smecton SA (Kunimine Industries, CEC: 100 meq/100 g) to 500 g of water and by dispersing the clay well. An aqueous solution (400 g) containing 2 equivalents of poly (diallyldimethylammonium chloride) (PDDA) (Aldrich, low molecular grade) with respect to the CEC of Smecton SA was added to the aqueous dispersion of the clay, and the mixture was blended by stirring at room temperature for 6 hours. To this was added 100 g of a BB aqueous solution containing 0.5 equivalents of Brilliant Blue FCF (BB) with respect to the CEC of Smecton SA, and the mixture was blended by stirring at room temperature for 1 day. Then the mixture was centrifuged (12000 rpm×30 min), washed, and dried (70° C.) to obtain the powder of BB-intercalating clay mineral (BB/PDDA/SU-1). The obtained BB/PDDA/SU-1 was blue, and its ζ-potential was +30.4 mV, showing a positive surface potential.

EXAMPLE 2-2

The powder of BB-intercalating clay mineral (BB/PDDA/La-1) was obtained by a similar treatment to that of Example 2-1 except for the use of Laponite XLG (Laporte Industries, CEC: 66 meq/100 g) instead of Smecton. The obtained BB/PDDA/La-1 was blue, and its ζ-potential was +31.3 mV, showing a positive surface potential.

Interlayer Distance

In order to investigate whether the polybase PDDA or the acid dye BB is intercalated between the layers of the water-swellable clay mineral or not, the interlayer distance was measured by XRD analysis (JDX-3500, JEOL). In Examples 1 and 2, a portion of the mixed solution before the addition of acid dye was sampled to obtain PDDA/clay powder (PDDA/SU-1 and PDDA/La-1), and a portion of BB-intercalating clay mineral before washing was also sampled to obtain non-washed BB-intercalating clay mineral. These were also measured by XRD analysis, and the results are shown in FIG. 4.

Figure 4:
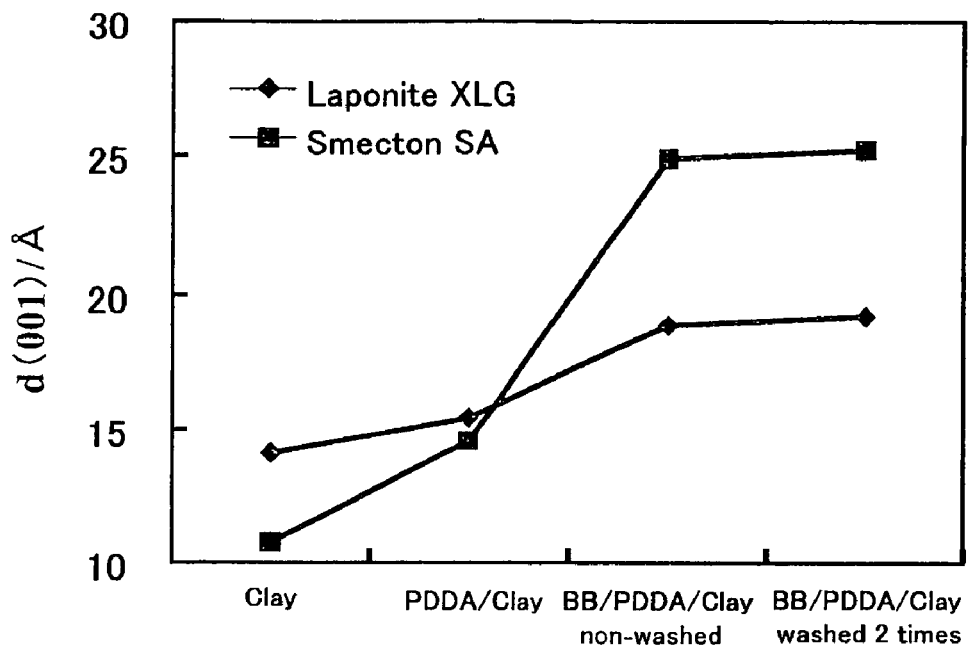
FIG. 4 shows the variation of the interlayer distance, with the intercalation of polybase (PDDA) and acid dye (BB) between the layers of water-swellable clay mineral (SU or La), in the acid dye/water-swellable clay mineral complex (Examples 2-1 or 2-2), which is one example of the present invention.

As shown in FIG. 4, the d-value of the peak assigned to (001) plane of Smecton SA increased from 10.8 Å (SU), which is the value before the intercalation of PDDA, to 14.48 Å (PDDA/SU-1), which is the value after the intercalation of PDDA. Thus, it was confirmed that PDDA is intercalated between the layers. After the intercalation of Brilliant Blue FCF, it further increased to 23.84 Å (BB/PDDA/SU-1). Thus, it was confirmed that Brilliant Blue FCF was also intercalated between the layers.

When Laponite XLG was used as a host, the d-value of the peak assigned to (001) plane increased from 14.1 Å (La), which is the value before the intercalation of PDDA, to 15.4 Å (PDDA/La-1), which is the value after the intercalation of PDDA. After the intercalation of Brilliant Blue FCF, it further increased to 18.78 Å (BB/PDDA/La-1). Thus, it was confirmed that PDDA and Brilliant Blue FCF are intercalated between the layers.

In both cases, a change in the interlayer distance due to washing was hardly observed. Thus, it was considered that both polybase PDDA and acid dye BB were strongly intercalated between the layers of the water-swellable clay mineral.

Elemental Analysis and Amount of Adsorbed Dye

The elemental analysis, for C, H, and N, of the obtained acid dye/water-swellable clay mineral complex was conducted with a 2400II CHNS/O (PerkinElmer) analyzer. In addition, from the elemental analysis results of C, H, and N, the amount of adsorbed dye in the acid dye/water-swellable clay mineral complex was calculated. The results are shown in Table 9.

TABLE 9

| Samples | % C (n = 2) | Adsorbed Dye (wt %) |
|---|---|---|
| PDDA/SU-1 | 10.51 | — |
| BB/PDDA/SU-1 | 22.30 | 23.6 |
| PDDA/La-1 | 9.78 | — |
| BB/PDDA/La-1 | 16.26 | 13.0 |

As is clear from Table 9, the carbon content in PDDA/Clay has increased, and the carbon content in BB/PDDA/Clay has further increased. The results support the above XRD analysis results that the polybase PDDA and the acid dye BB are intercalated between the layers. The amount of intercalated dye calculated from the carbon content (% C) was 23.6% for Smecton and 13.0% for Laponite, showing very high values. When the host was Laponite, the amount of contained dye was smaller than that of Smecton. This is probably because of the smaller CEC of Laponite than the CEC of Smecton.

EXAMPLE 2-3

An aqueous dispersion of the clay was obtained by adding 5 g of Smecton SA (Kunimine Industries, CEC: 100 meq/100 g) to 500 g of water and by dispersing the clay well. An aqueous solution (400 g) containing 2 equivalents of poly (diallyldimethylammonium chloride) (PDDA) (Aldrich, low molecular grade) with respect to the CEC of Smecton SA was added to the aqueous dispersion of the clay, and the mixture was blended by stirring at room temperature for 6 hours. Then the mixture was centrifuged (12000 rpm×30 min) and washed twice to obtain PDDA-intercalating water-swellable clay mineral.

The obtained PDDA-intercalating water-swellable clay mineral was dispersed again in 900 g of water. To this was added 100 g of a BB aqueous solution containing 0.5 equivalents of Brilliant Blue FCF (BB) with respect to the CEC of Smecton SA, and the mixture was blended by stirring at room temperature for 1 day. Then the mixture was centrifuged (12000 rpm×30 min), washed, and dried (70° C.) to obtain the powder of BB-intercalating clay mineral (BB/PDDA/SU-2). The obtained BB/PDDA/SU-2 was blue, and its $\zeta$-potential was +27.5 mV, showing a positive surface potential. The carbon content (% C) was 18.15% by CHN elemental analysis, and the amount of adsorbed dye in the powder was 15.3%.

COMPARATIVE EXAMPLES 2-1 AND 2-2

An aqueous dispersion of the clay was obtained by adding 3 g of Smecton SA or Laponite XLG to 100 g of water and by dispersing the clay well. This was mixed with 100 g of an aqueous solution containing 0.3 g of Brilliant Blue FCF (BB), and the pH of the mixed solution was adjusted with hydrochloric acid to 3 or 6.5. Then, the mixture was stirred at room temperature for 1 day, centrifuged (18000 rpm×1 h), washed three times, and dried at 60° C. The interlayer distance of the obtained powder was measured in the same way as above. The results are shown in FIG. 5.

Figure 5:
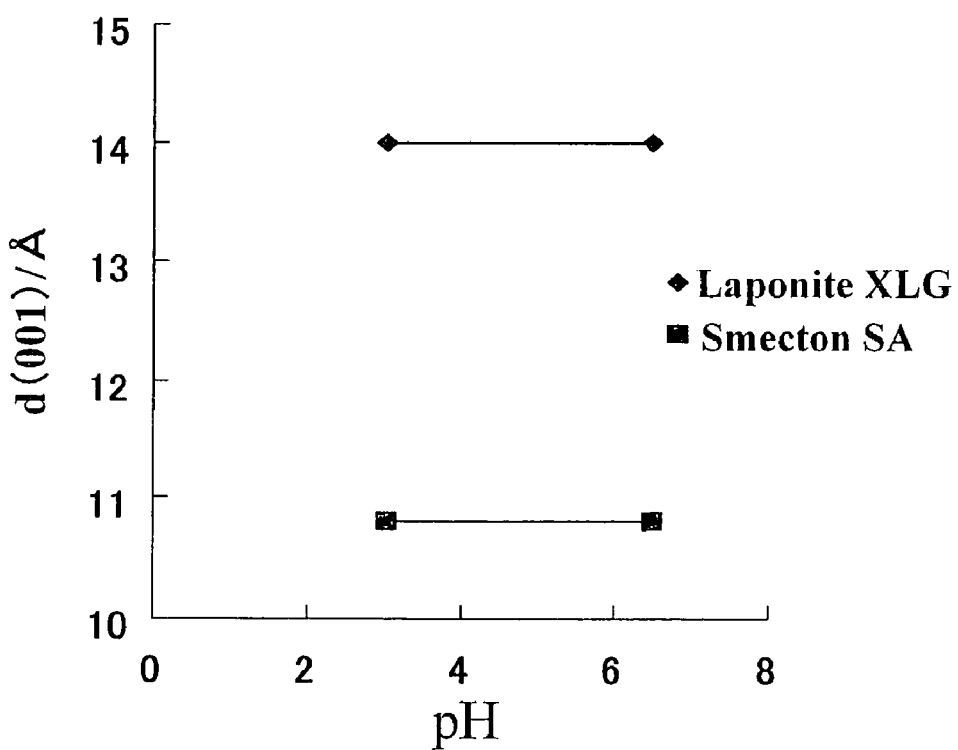
FIG. 5 shows the interlayer distance at each pH when water-swellable clay mineral and acid dye were mixed without polybase (Comparative Example 2-1).

As is clear from FIG. 5, an increase in the interlayer distance, from that of the untreated clay (SU: 10.8 Å, La: 14.1 Å), was not observed at any pH. Thus, it is clear that it is difficult to directly intercalate the acid dye BB between the layers of the water-swellable clay mineral.

EXAMPLE 2-4

BB/PDDA/SU-1 (ca. 0.5 g) obtained in Example 2-1 was added to 100 g of water and dispersed well. To this was added, as a base powder, pigment grade titanium dioxide (Kerr-McGee Tronox R-KB-2, average primary particle diameter: 0.3 µm, $\zeta$-potential: −21.2 mV). The amount of the titanium dioxide was approximately three times, in weight ratio, of BB/PDDA/SU-1. Then the mixture was stirred at room temperature for 24 hours, centrifuged, washed, and dried at 70° C. to obtain the powder of titanium dioxide coated with BB-intercalating clay mineral (BB/PDDA/SU/TiO2-1). The obtained BB/PDDA/SU/TiO2-1 was blue.

EXAMPLE 2-5

The powder of pearlescent pigment coated with BB-intercalating clay mineral (BB/PDDA/SU/TSL-1) was obtained in the same way as Example 2-4 using a white pearlescent pigment (Merck, Timiron MP115 Starluster, primary particle diameter: 10 to 60 µm, $\zeta$-potential: −31.7 mV) as the base powder. The obtained BB/PDDA/SU/TSL-1 was blue.

EXAMPLE 2-6

The powder of the pearlescent pigment coated with BB-intercalating clay mineral (BB/PDDA/La/TSL-1) was obtained ($\zeta$-potential: +20.4 mV) in the same way as Example 2-5 except that BB/PDDA/La-1 obtained in Example 2-2 was used, as an acid dye/water-swellable clay mineral complex, instead of BB/PDDA/SU-1.

This powder was dispersed in a 1% aqueous solution of a polyanion, polystyrene sulfonic acid (PSS), filtered, and washed to obtain PSS coated BB/PDDA/La/TSL-1 [PSS/(BB/PDDA/La/TSL-1)] ($\zeta$-potential: −33.2 mV).

This was further added to an aqueous dispersion of the above BB/PDDA/La-1 (Example 2-2) at a concentration where gelation does not take place. The mixture was blended by stirring, filtered, and washed to obtain (BB/PDDA/La/PSS)/(BB/PDDA/La/TSL-1). In addition, a series steps from the above PSS coating process were repeated four times to obtain the pearlescent pigment (BB/PDDA/La/PSS)$_5$/(BB/PDDA/La/TSL-1), which has six layers of coated BB/PDDA/La-1. The obtained pigment powder was blue.

EXAMPLE 2-7

Five parts of methyl hydrogen polysiloxane was added to 100 parts of BB/PDDA/SU/TiO2-1, which was obtained in Example 2-4, and mixed with a Henschel mixer to obtain silicone-treated BB/PDDA/SU/TiO2-1. Color change was not observed by this hydrophobic treatment.

The carbon content (% C) and the amount of adsorbed dye in each laminate (from Example 2-4 to Example 2-6) are shown in Table 10.

TABLE 10

| Samples | % C (n = 2) | Adsorbed dye (wt %) |
| --- | --- | --- |
| BB/PDDA/SU/TiO2-1 | 3.61 | 3.85 |
| BB/PDDA/SU/TSL-1 | 3.44 | 3.68 |
| (BB/PDDA/La/PSS)$_5$/(BB/PDDA/La/TSL-1) | 20.33 | 20.04 |

As shown in Table 10, the amount of dye coated on the base powder was 3.85 wt % when the base powder was pigment grade titanium dioxide, and was 3.68 wt % when the base powder was white pearlescent pigment. When the white pearlescent pigment was coated six times, the amount of dye was 20.04 wt %. Thus, the amount of coated BB-intercalating clay mineral increased with an increase in the number of laminatied layers.

Figure 6:
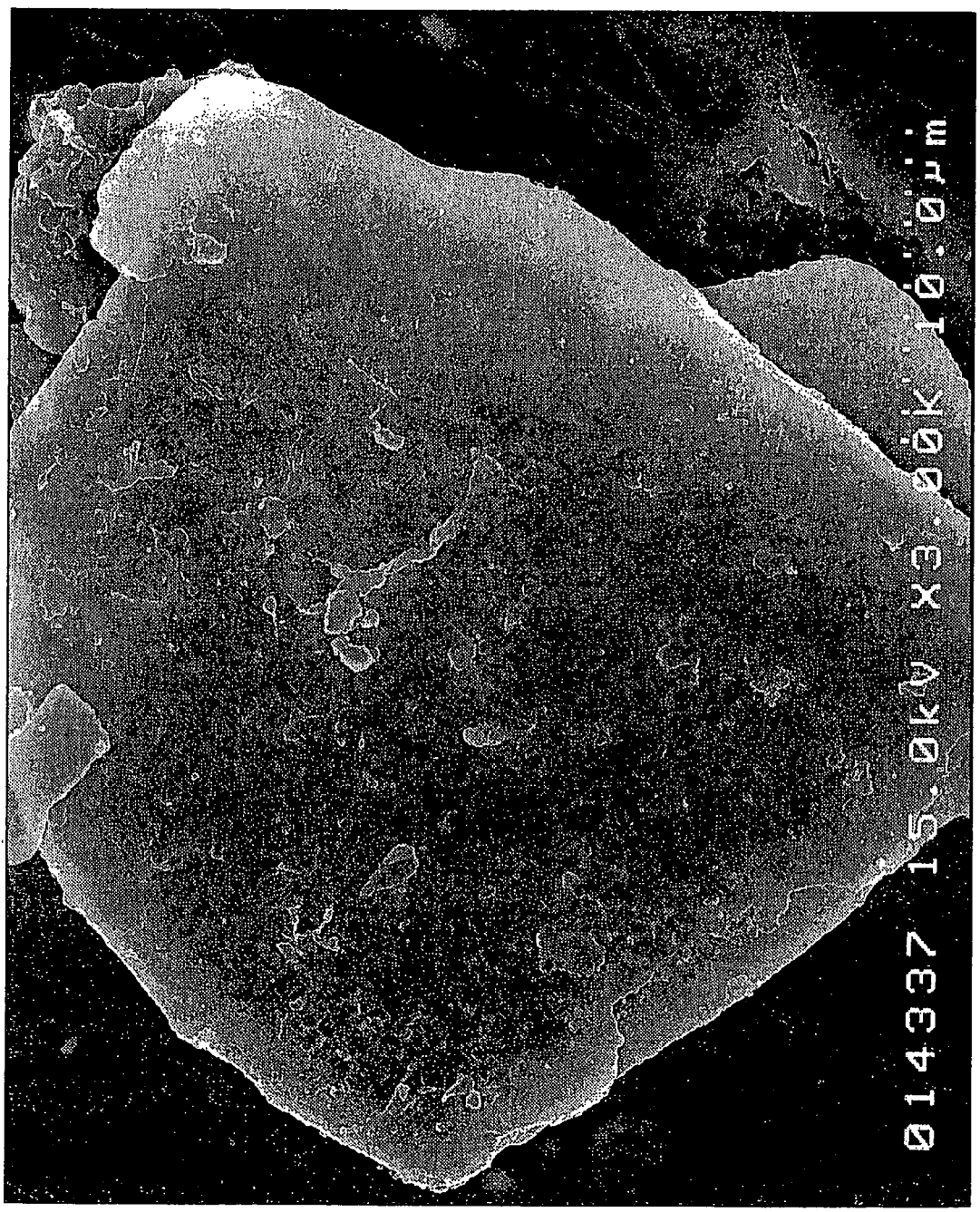
FIG. 6 shows an SEM image of the acid dye laminate pigment (Example 2-5), which is one example of the present invention.

FIG. 6 shows an SEM image of the BB/PDDA/SU/TSL-1 obtained in Example 2-5. In the figure, the surface of the base powder is completely covered with the BB-intercalating water-swellable clay mineral (BB/PDDA/SU-1). In SEM images of BB/PDDA/SU/TiO2-1 in Example 2-4 and (BB/PDDA/SU/PSS)$_5$/(BB/PDDA/SU/TSL-1) in Example 2-6, the base powder was also completely covered.

Dissolution Resistance

BB/PDDA/SU/TSL-1 in Example 2-5 and BB/PDDA/SU/TiO2-1 in Example 2-4 were respectively dispersed in ion-exchanged water so that the concentration is 0.01%. After the dispersion was stirred for 60 minutes, the supernatant liquid was sampled and the apparent color of the supernatant liquid was observed. For comparison, the same observation was conducted for Brilliant Blue A1 lake (BB-A1). The results are shown in Table 11.

TABLE 11

| Samples | Color of supernatant liquid |
| --- | --- |
| (BB/PDDA/SU)/TSL-1 | Clear and colorless |
| (BB/PDDA/SU)/TiO2-1 | Clear and colorless |
| BB-Al | Clear and blue |

As shown in Table 11, the supernatant liquid of the Al lake of BB was blue, and the dye dissolved into water. In contrast, the supernatant liquid of both acid dye laminated pigments of the present invention was clear and colorless, and the dissolution of the dye into the supernant liquid was not observed at all.

Thus, the acid dye laminated pigment of the present invention has excellent dissolution resistance.

Lightfastness of Acid Dye Laminated Pigment

Eye shadow was prepared according to the formulation in Table 12 using BB/PDDA/SU/TiO2-1 in Example 2-4 or BB-A1 as a pigment. That is, powder components and oil components were mixed in a Henschel mixer, pulverized twice with a pulverizer, packed in a container (medium resin plate), and molded with a dry press according to the conventional method.

The obtained eye shadow was illuminated with a Xe lamp (50° C.×10 h), and the color difference before and after the Xe illumination was measured. The results are shown in Table 12.

| Components | Formulation Example 2-1 | Comparative Example 2-1 |
| --- | --- | --- |
| BB/PDDA/SU/TiO2-1 | 3 | — |
| BB-Al | — | 3 |
| Talc | to 100 | to 100 |
| Mica | 10.5 | 10.5 |
| Spherical PMMA | 2 | 2 |
| Boron nitride | 1 | 1 |
| Liquid paraffin | 4 | 4 |
| Dimethicone | 4 | 2 |
| Sorbitan sesquiisostearate | 0.8 | 0.8 |
| Paraben | q.s. | q.s. |
| Antioxidant | q.s. | q.s. |
| Perfume | q.s. | q.s. |
| Color difference ΔE | 6.8 | 11.3 |

As seen from Table 12, the acid dye laminated pigments of the present invention have excellent lightfastness compared with the conventional BB-A1 lake.

Lightfastness of Acid Dye/Water-swellable Clay Mineral Complex

The lightfastness of acid dye/water-swellable clay mineral complexes obtained in the present invention was also investigated Aqueous dispersions (powder concentration: 0.1%) of BB/PDDA/SU-1 obtained in Example 2-1 and BB/PDDA/La-1 obtained in Example 2-2 were illuminated with a Xe lamp at 50° C. for 30 hours. There was no change in apparent color, indicating the lightfastness of these complexes.

Chlorine Resistance

The chlorine resistance was investigated for aqueous dispersions of acid dye/water-swellable clay mineral complexes of the present invention.

(Samples)
(1) BB/PDDA/La-1 (Powder obtained in Example 2-2)
(2) RB/PDDA/La-1 (Powder obtained in the same way as Example 2-2 except that Resorcin Brown (RB, Brown No. 201) was used instead of BB.)

(Test Method)

The acid dye BB and acid dye RB were added, respectively, to water of 0 ppm free chlorine concentration so that the concentration of the solution is 0.4 ppm. These aqueous solutions are used as the control of BB and the control of RB. The sample solutions were prepared by dissolving sample powders, respectively, into water of 0 ppm free chlorine concentration so that the apparent color is similar to that of each control.

To both control and sample solutions was added hydrochloric acid so that the concentration of the free chlorine is x ppm. The L, a, b, values were measured before and after the addition of hydrochloric acid (instrument for measurement: Gretag Macbeth Color-Eye 7000A). From the measured values, the color difference between the added system with x ppm chlorine concentration and the system with 0 ppm chlorine, $\Delta E_{x-0}$, was calculated. The smaller the color difference ($\Delta E_{x-0}$) is, the higher the chlorine resistance.

The results are shown in Table 13.

TABLE 13

| Added Dye | Cl(ppm) | L | a | b | ΔEx-0 |
| --- | --- | --- | --- | --- | --- |
| BB 0.4 ppm | 0 | 98.615 | −3.032 | −1.662 | — |
|  | 0.5 | 98.826 | −0.941 | −0.958 | 2.216 |
|  | 1 | 98.978 | −0.863 | −0.835 | 2.350 |
| BB/PDDA/La-1 | 0 | 98.742 | −2.624 | −1.327 | — |
|  | 0.5 | 99.019 | −1.602 | −0.921 | 1.134 |
|  | 1 | 99.302 | −1.267 | −0.638 | 1.622 |
| RB 0.4 ppm | 0 | 98.844 | −0.164 | 4.215 | — |
|  | 0.5 | 99.539 | −0.019 | 0.179 | 4.098 |
|  | 1 | 99.411 | −0.008 | 0.195 | 4.063 |
| RB/PDDA/La-1 | 0 | 99.15 | −0.018 | 3.043 | — |
|  | 0.5 | 99.791 | 0.029 | 0.355 | 2.764 |
|  | 1 | 99.957 | −0.013 | 0.065 | 3.085 |

As is clear from Table 13, compared with the aqueous solution of the acid dye BB or the acid dye RB itself, the aqueous solution of acid dye/water-swellable clay mineral complex, BB/PDDA/La-1 or RB/PDDA/La-1 of the present invention had smaller $\Delta E_{x-0}$ values, indicating better chlorine resistance.

The L values of the aqueous solutions of acid dye/water-swellable clay mineral complexes of the present invention are close to 100% as well as that of each control, indicating high transparency. The coloring abilities also were excellent.

2-2 Water-Soluble Dye/Water-Swellable Clay Mineral Complex

Preparation of Water-soluble Dye/Nonionic Hydrophilic Polymer/Water-swellable Clay Mineral Complex

EXAMPLE 2-8

An aqueous dispersion of the clay was obtained by adding 4 g of Laponite XLG (Laporte Industries, CEC: 66 meq/100 g) (La) to 250 g of water and by dispersing the clay well. To the above aqueous dispersion was added 90 g of 17% PVP aqueous solution, and the mixture was blended by stirring at room temperature for 1 day. To a 50 g portion of this mixed solution was added 90 g of an aqueous solution containing one equivalent of Brilliant Blue FCF (BB) with respect to the CEC of Laponite XLG, and the mixture was blended by stirring at room temperature for 1 day. Then the mixture was centrifuged (18000 rpm×1.5 h) to obtain the powder of BB-intercalating clay mineral (BB/PVP/La-1). The obtained BB/PVP/La-1 was blue.

EXAMPLE 2-9

An aqueous dispersion of the clay was obtained by adding 4 g of Laponite XLG (Laporte Industries, CEC: 66 meq/100 g) (La) to 250 g of water and by dispersing the clay well. To the above aqueous dispersion was added 90 g of 17% PVP aqueous solution, and the mixture was blended by stirring at room temperature for 1 day. To a 50 g portion of this mixed solution was added 90 g of an aqueous solution containing one equivalent of Resorcin Brown (RB) with respect to the CEC of Laponite XLG, and the mixture was blended by stirring at room temperature for 1 day. Then the mixture was centrifuged (12000 rpm×0.5 h) to remove a precipitate once. It was further centrifuged (18000 rpm×1.5 h) to obtain the powder of RB-intercalating clay mineral (RB/PVP/La-1). The obtained RB/PVP/La-1 was blue.

Chlorine Resistance

The chlorine resistance was investigated for aqueous dispersions of water-soluble dye/water-swellable clay mineral complexes of the present invention.

(Test Method)

The acid dye RB was added to water of 0 ppm free chlorine concentration so that the concentration of the solution is 0.4 ppm. This aqueous solution was used as the RB control. The sample solutions were, respectively, prepared by dissolving the water-soluble dye/water-swellable clay mineral complex powder of Example 2-9 into water of 0 ppm free chlorine concentration so that the apparent color is similar to that of the control.

To both control and sample solutions was added hydrochloric acid so that the concentration of the free chlorine is x ppm. The L, a, b, values were measured before and after the addition of hydrochloric acid (instrument for measurement: Gretag Macbeth Color-Eye 7000A). From the measured values, the color difference between the added system with x ppm chlorine concentration and the system with 0 ppm chlorine, $\Delta E_{X-0}$, was calculated. The smaller the color difference ($\Delta E_{X-0}$) is, the higher the chlorine resistance. The results are shown in Table 14.

TABLE 14

| AddedDye | Cl(ppm) | L | a | b | ΔEx-0 |
|---|---|---|---|---|---|
| RB 0.4 ppm | 0 | 99.176 | −0.163 | 4.082 | — |
| | 0.5 | 99.992 | −0.027 | 0.148 | 4.020 |
| | 1 | 100.041 | −0.012 | 0.154 | 4.025 |
| RB/PVP/La-1 | 0 | 99.128 | −0.076 | 4.01 | — |
| | 0.5 | 99.567 | 0.031 | 1.428 | 2.621 |
| | 1 | 99.762 | 0.032 | 0.431 | 3.636 |

As is clear from Table 14, compared with the aqueous solution of the water-soluble dye RB itself, the aqueous solution of water-soluble dye/water-swellable clay mineral complex (RB/PVP/La-1) of the present invention had smaller $\Delta E_{X-0}$ values, indicating better chlorine resistance.

The L values of the aqueous solutions of the water-soluble dye/water-swellable clay mineral complex of the present invention are close to 100% as well as that of the control, indicating high transparency. The coloring abilities also were excellent.

FORMULATION EXAMPLE 2-1

Dual-use Foundation

| (1) Silicone-treated talc | to 100 |
|---|---|
| (2) Silicone-treated sericite | 20 |
| (3) Silicone-treated mica | 10 |
| (4) Silicone-treated titanium oxide | 10 |
| (5) Silicone-treated red iron oxide | 0.8 |
| (6) Silicone-treated yellow iron oxide | 3 |
| (7) Silicone-treated black iron oxide | 0.2 |
| (8) BB/PDDA/SU/TSL-1 | 3 |
| (9) Liquid paraffin | 4 |
| (10) Vaseline | 4 |
| (11) Sorbitan sesquiisostearate | 0.8 |
| (12) Preservative | q.s. |
| (13) Antioxidant | q.s. |
| (14) Perfume | q.s. |

Preparation

Powder components and oil components in the formulation were mixed in a Henschel mixer, pulverized twice with a pulverizer, packed in a container (medium resin plate), and molded with a dry press according to the conventional method.

FORMULATION EXAMPLE 2-2

Single-use Foundation

| (1) Talc | to 100 |
|---|---|
| (2) Sericite | 20 |
| (3) Mica | 10 |
| (4) Titanium oxide | 10 |
| (5) Red iron oxide | 0.8 |
| (6) Yellow iron oxide | 3 |
| (7) Black iron oxide | 0.2 |
| (8) (BB/PDDA/SU/PSS)$_5$/(BB/PDDA/SU/TSL-1) | 3 |
| (9) (Tartrazine/PDDA/SU)/TiO2 | 0.1 |
| (10) (BB/PDDA/SU)/TiO2-1 | 0.1 |
| (11) Liquid paraffin | 4 |
| (12) Vaseline | 4 |
| (13) Sorbitan sesquiisostearate | 0.8 |
| (14) Preservative | q.s. |
| (15) Antioxidant | q.s. |
| (16) Perfume | q.s. |

Preparation

This was prepared in a similar way to Formulation Example 2-1.

FORMULATION EXAMPLE 2-3

Face Powder

| (1) Mica | 10 |
|---|---|
| (2) Talc | to 100 |
| (3) Zinc oxide | 5 |
| (4) Fine titanium oxide | 3 |
| (5) BB/PDDA/TiO2-1 | 0.1 |

-continued

| | | |
|---|---|---|
| (6) Violamine R/PDDA/TiO2 | 0.1 | |
| (7) Fluorphlogopite | 10 | |
| (8) Vaseline | 1 | |
| (9) Squalane | 2 | |
| (10) Ester oil | 1 | |
| (11) Preservative | q.s. | |
| (12) Antioxidant | q.s. | |
| (13) Perfume | q.s. | |

Preparation

This was prepared in a similar way to Formulation Example 2-1.

FORMULATION EXAMPLE 2-4

Pre-makeup Lotion

| | | |
|---|---|---|
| Oil phase | | |
| (1) Decamethyl cyclopenta siloxane | to 100 | |
| (2) Polyether-modified silicone | 3 | |
| (3) Silicone-treated BB/PDDA/SU/TSL-1 | 3 | |
| (4) Trimethyl siloxysilicate | 2 | |
| Water phase | | |
| (5) 1,3-Butylene glycol | 5 | |
| (6) Dynamite glycerin | 2 | |
| (7) Preservative | 0.5 | |
| (8) Purified water | 30 | |

Preparation

The water phase was added to the oil phase, which had been heated to 70° C., and the mixture was sufficiently emulsified with an emulsifying machine. The obtained emulsion was cooled with stirring to less than 35° C., poured into a container, and allowed to cool to obtain the desired pre-makeup lotion.

FORMULATION EXAMPLE 2-5

Eye Shadow

| | | |
|---|---|---|
| (1) Talc | balance | |
| (2) Sericite | 7 | |
| (3) Mica | 15 | |
| (4) Spherical PMMA powder | 3 | |
| (5) Tartrazine/PDDA/SU/TiO2 | 10 | |
| (6) Barium sulfate | 4 | |
| (7) Iron oxide | 1.5 | |
| (8) Squalane | 2 | |
| (9) Dimethylpolysiloxane | 2 | |
| (10) Sorbitan monooleate | 0.5 | |
| (11) Preservative | q.s. | |
| (12) Perfume | q.s. | |

Preparation

Powder components and oil components in the formulation were mixed in a Henschel mixer, pulverized twice with a pulverizer, packed in a container (medium resin plate), and molded with a dry press according to the conventional method.

FORMULATION EXAMPLE 2-6

Oil Stick

| | | |
|---|---|---|
| (1) Carnauba wax | 1 | |
| (2) Candelilla wax | 2 | |
| (3) Ceresin | 10 | |
| (4) Squalane | balance | |
| (5) Glyceryl triisooctanoate | 9 | |
| (6) Glyceryl diisostearate | 13 | |
| (7) Dimethylpolysiloxane (viscosity: 90,000 mPa·s at 25° C.) | 5 | |
| (8) Dimethylpolysiloxane (viscosity: 1.000 mPa·s at 25° C.) | 5 | |
| (9) Silicone resin | 8 | |
| (10) Hydroxypropyl-β-cyclodextrin | 1 | |
| (11) Cholesteryl macadamiate | 3.5 | |
| (12) Synthetic sodium magnesium silicate | 0.5 | |
| (13) Hydrophobic silica | 0.5 | |
| (14) Purified water | 2 | |
| (15) Spherical silicone resin powder coated mica | 3 | |
| (16) Silicone-treated (BB/PDDA/SU1)/TSL-1 | 5 | |
| (17) Barium sulfate | 3 | |
| (18) Coloring material | q.s. | |
| (19) Preservative | q.s. | |
| (20) Perfume | q.s. | |

Preparation

Components 12 to 13 were dispersed in component 11, which had been heated to 60° C., and to the mixture was added uniformly dissolved components 10 and 14 and stirred well. The above mixture was added to components 1 to 9, which had been dissolved under heating, and stirred well. Then components 15 to 20 were added to the mixture and dispersed; the product was filled into a container to obtain an oil stick.

FORMULATION EXAMPLE 2-7

Cream

| | | |
|---|---|---|
| Oil phase | | |
| (1) Decamethyl cyclopenta siloxane | 10.5 | |
| (2) Dimethylpolysiloxane (6 CS/25° C.) | 4.0 | |
| (3) Stearyl alcohol | 1.5 | |
| (4) Vaseline | 5.0 | |
| (5) Squalane | 1.0 | |
| (6) Vitamin E acetate | 0.01 | |
| (7) Violamine R/PDDA/SU/TiO2 | 5.0 | |
| (8) Polyether-modified silicone | 2.0 | |
| Water phase | | |
| (9) Preservative | 0.2 | |
| (10) 1,3-Butylene glycol | 17.0 | |
| (11) Purified water | balance | |

Preparation
The cream was prepared by the conventional method.

FORMULATION EXAMPLE 2-8

Sunscreen Lotion

| Oil phase | |
|---|---|
| (1) Dimethylpolysiloxane (6 CS/25° C.) | 5.0 |
| (2) Dimethylpolysiloxane (1.5 CS/25° C.) | 13.0 |
| (3) Phenyl-modified methylphenylpolysiloxane | 3.0 |
| (4) Violamine R/PDDA/SU/TSL | 5.0 |
| (5) Polyether-modified silicone | 2.0 |
| Water phase | |
| (6) Sodium chloride | 9.0 |
| (7) Perfume | 0.2 |
| (8) Preservative | 0.2 |
| (9) Ethanol | 5.0 |
| (10) Purified water | balance |

Preparation
The sunscreen lotion was prepared by the conventional method.

FORMULATION EXAMPLE 2-9

Liquid Emulsion Foundation

| Oil phase | |
|---|---|
| (1) Decamethyl cyclopenta siloxane | balance |
| (2) Trimethyl siloxysilicate | 3.0 |
| (3) Dimethylpolysiloxane | 5.0 |
| (4) Dimethylpolysiloxane polyoxyalkylene copolymer | 2.5 |
| (5) Sorbitan sesquiisostearate | 2.0 |
| Powder components | |
| (6) Silicone-treated talc | 5.0 |
| (7) Silicone-treated titanium dioxide | 5.0 |
| (8) (BB/PDDA/SU)/TSL-1 | 5.5 |
| (9) Silicone-treated nylon powder | 4.0 |
| (10) Silicone-treated coloring pigment | 2.0 |
| Water phase | |
| (11) 1,3-Butylene glycol | 3.0 |
| (12) Ethanol | 13.0 |
| (13) Purified water | 10.0 |

Preparation
Powder components were added to the oil phase, which had been heated to 70° C. and had been stirred. Then the mixture was dispersed with a homomixer at 70° C. and cooled to room temperature. To this was added the water phase, and the mixture was emulsified with the homomixer to obtain the liquid foundation.

FORMULATION EXAMPLE 2-10

Creamy Emulsion Foundation

| Oil phase | |
|---|---|
| (1) Decamethyl cyclopenta siloxane | balance |
| (2) Trimethyl siloxysilicate | 3.0 |
| (3) Dimethylpolysiloxane | 5.0 |
| (4) Sorbitan sesquiisostearate | 2.0 |
| (5) Dimethylpolysiloxane polyoxyalkylene copolymer | 3.5 |
| (6) Dimethylstearylammonium hectorite | 2.0 |
| Powder components | |
| (7) Silicone-treated talc | 5.0 |
| (8) Silicone-treated titanium dioxide | 5.0 |
| (9) Silicone-treated (BB/PDDA/SU)/TiO2 | 2.0 |
| (10) Silicone-treated nylon powder | 4.0 |
| Water phase | |
| (11) 1,3-Butylene glycol | 3.0 |
| (12) Ethanol | 20.0 |
| (13) Purified water | 20.0 |

Preparation
The creamy foundation was prepared according to the method of Formulation Example 2-9.

FORMULATION EXAMPLE 2-11

Nail Enamel

| | |
|---|---|
| (1) Nitrocellulose HIG ½ sec. | 10 |
| (2) Nitrocellulose HIG ¼ sec. | 5 |
| (3) Alkyd resin | 10 |
| (4) Acetyl tributyl citrate | 5 |
| (5) Ethyl acetate | 25 |
| (6) n-Butyl acetate | to 100 |
| (7) n-Butyl alcohol | 5 |
| (8) (BB/PDDA/SU)/TSL-1 | 2 |

Preparation
The nail enamel was prepared by the conventional method.

FORMULATION EXAMPLE 2-12

Lotion

| | |
|---|---|
| (1) Ion-exchanged water | balance |
| (2) Ethanol | 10 |
| (3) Di(propylene glycol) | 10 |
| (4) PEG1500 | 5 |
| (5) POE (20) oleyl alcohol ether | 0.5 |
| (6) Methylcellulose | 0.3 |
| (7) Preservative | 0.2 |
| (8) Chelating agent | 0.01 |
| (9) Perfume | q.s. |
| (10) BB/PDDA/La-1 | 0.01 |

Preparation
Components 3, 4, 6, and 8 were dispersed in a portion of component 1. Then to the dispersion were added components 5, 7, and 9 dissolved in component 2. Component 10 was dispersed in the rest of component 1, and the mixture was stirred until it became clear. The obtained colored solution was added to the above mixed solution to adjust the color, and the solution was filtered to obtain the lotion.

FORMULATION EXAMPLE 2-13

Milky Lotion

| Oil components | |
|---|---|
| (1) Dimethicone | 5 |
| (2) Cyclomethicone | 5 |
| (3) Liquid paraffin | 5 |
| Moisturizer | |
| (4) Glycerin | 4 |
| (5) 1,3-Butylene glycol | 5 |
| Polymers | |
| (6) Carboxyvinyl polymer | 0.1 |
| (7) Acrylic acid/methacrylic acid acrylic copolymer | 0.1 |
| Neutralizer | |
| (8) Potassium hydroxide | q.s. |
| Coloring Agent | |
| (9) Tartrazine/PDDA/La | 0.01 |
| (10) Preservative | q.s. |
| (11) Antioxidant | q.s. |
| (12) Perfume | q.s. |
| (13) Ion-exchanged water | balance |

Preparation

To moisturizer components and preservative, which had been dissolved in a portion of ion-exchanged water under heating, was added polymer components and dissolved at room temperature. To the mixture is added neutralizer to obtain a water phase. To the water phase is added oil components, which had been uniformly mixed at room temperature, antioxidant, and perfume, and the mixture was emulsified with a homomixer. Then, to the emulsion was added a clear colored solution obtained, in advance, by dispersing tartrazine/PVP/La in the rest of ion-exchanged water. The mixture was blended by stirring to adjust the color, deaerated, and filtered to obtain the milky lotion.

FORMULATION EXAMPLE 2-14

Lotion

| (1) Ion-exchanged water | balance |
|---|---|
| (2) Ethanol | 10 |
| (3) Di(propylene glycol) | 10 |
| (4) PEG1500 | 5 |
| (5) POE (20) oleyl alcohol ether | 0.5 |
| (6) Methylcellulose | 0.3 |
| (7) Preservative | 0.2 |
| (8) Chelating agent | 0.01 |
| (9) Perfume | q.s. |
| (10) BB/PVP/La-1 | 0.01 |

Preparation

Components 3, 4, 6, and 8 were dispersed in a portion of component 1. Then to the dispersion were added components 5, 7, and 9 dissolved in component 2. Component 10 was dispersed in the rest of component 1, and the mixture was stirred until it became clear. The obtained colored solution was added to the above mixed solution to adjust the color, and the solution was filtered to obtain the lotion.

FORMULATION EXAMPLE 2-15

Milky Lotion

| Oil components | |
|---|---|
| (1) Dimethicone | 5 |
| (2) Cyclomethicone | 5 |
| (3) Liquid paraffin | 5 |
| Moisturizer | |
| (4) Glycerin | 4 |
| (5) 1,3-Butylene glycol | 5 |
| Polymers | |
| (6) Carboxyvinyl polymer | 0.1 |
| (7) Acrylic acid/methacrylic acid acrylic copolymer | 0.1 |
| Neutralizer | |
| (8) Potassium hydroxide | q.s |
| Coloring Agent | |
| (9) Tartrazine/PVP/La | 0.01 |
| (10) Preservative | q.s |
| (11) Antioxidant | q.s |
| (12) Perfume | q.s |
| (13) Ion-exchanged water | balance |

Preparation

To moisturizer components and preservative, which had been dissolved in a portion of ion-exchanged water under heating, was added polymer components and dissolved at room temperature. To the mixture is added neutralizer to obtain a water phase. To the water phase is added oil components, which had been uniformly mixed at room temperature, antioxidant, and perfume, and the mixture was emulsified with a homomixer. Then, to the emulsion was added a clear colored solution obtained, in advance, by dispersing tartrazine/PVP/La in the rest of ion-exchanged water. The mixture was blended by stirring to adjust the color, deaerated, and filtered to obtain the milky lotion.

What is claimed is:

1. An acid dye laminated pigment, in which a dye/water-swellable clay mineral complex, which having opposite charge to the charge of a base powder, is coated on the surface of the base powder, and a polybase and an acid dye are intercalated in between the layers of the water-swellable clay mineral of the dye/water-swellable clay mineral complex.

2. The acid dye laminated pigment according to claim 1, wherein one or more layer of the acid dye /water-swellable clay mineral complex is further laminated on the surface of the acid dye laminated pigment, and a layer of an ionic molecule, which having opposite surface charge to the charge of the acid dye/ water-swellable clay mineral complex, exists in between the each layers of the acid dye/ water-swellable clay mineral complex.

3. The acid dye laminated pigment according to claim 1 wherein the primary particle diameter of the water-swellable clay mineral is 1 µm or less.

4. The acid dye laminated pigment according to claim 1, wherein the average particle diameter of the base powder is 0.1 to 1000 µm.

5. The acid dye laminated pigment according to claim 1 wherein the surface of the acid dye laminated pigment is further treated to be hydrophobic.

6. A producing method of an acid dye laminated pigment comprising; an acid dye/water-swelling clay mineral complex producing process for an acid dye is intercalated in between the layers of the water-swellable clay mineral, wherein a polybase and an acid dye is contacted to a water-swellable clay mineral in aqueous phase; and laminating process for the acid dye/water-swelling clay mineral complex is electrostatically adsorbed on the surface of a base powder, wherein obtained acid dye/water-swelling clay mineral complex and a base powder, which having opposite charge to the charge of the complex, are mixed in aqueous phase.

7. A pigment composition comprising the acid dye laminated pigment according to claim 1.

8. A cosmetic comprising the acid dye laminated pigment according to claim 1.

* * * * *